US012661111B2

(12) United States Patent
Stout et al.

(10) Patent No.: US 12,661,111 B2
(45) Date of Patent: Jun. 23, 2026

(54) SURGICAL STAPLER HAVING CONTROLLABLE SHAFT BIAS

(71) Applicant: Cilag GmbH International, Zug (CH)

(72) Inventors: Eric D. Stout, Cincinnati, OH (US); Jonathan Z. Von Stein, Cincinnati, OH (US); Heather E. Dickson, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 181 days.

(21) Appl. No.: 18/758,277

(22) Filed: Jun. 28, 2024

(65) Prior Publication Data

US 2026/0000397 A1    Jan. 1, 2026

(51) Int. Cl.
A61B 17/00 (2006.01)
A61B 17/072 (2006.01)

(52) U.S. Cl.
CPC .. A61B 17/072 (2013.01); *A61B 2017/00075* (2013.01); *A61B 2017/00398* (2013.01); *A61B 2017/07278* (2013.01); *A61B 2017/07285* (2013.01)

(58) Field of Classification Search
CPC .... A61B 17/07207; A61B 2017/00017; A61B 2017/00398; A61B 17/07271; A61B 2017/07278; A61B 2017/07285; A61B 2090/0811; A61B 2017/00734
USPC ...................................................... 227/175.1
See application file for complete search history.

(56) References Cited

U.S. PATENT DOCUMENTS

| | | | |
|---|---|---|---|
| 6,988,649 | B2 | 1/2006 | Shelton, IV et al. |
| 8,012,170 | B2 | 9/2011 | Whitman et al. |
| 8,989,903 | B2 | 3/2015 | Weir et al. |
| 9,226,750 | B2 | 1/2016 | Weir et al. |
| 9,526,499 | B2 | 12/2016 | Kostrzewski et al. |
| 9,814,530 | B2 | 11/2017 | Weir et al. |
| 10,206,748 | B2 | 2/2019 | Burbank |

(Continued)

FOREIGN PATENT DOCUMENTS

CN        202982103 U       6/2013

OTHER PUBLICATIONS

U.S. Appl. No. 63/634,171, entitled "Robotic Stapling and Cutting Systems," filed Apr. 15, 2024.
(Continued)

*Primary Examiner* — Jacob A Smith
(74) *Attorney, Agent, or Firm* — FBT GIBBONS LLP

(57) ABSTRACT

A surgical instrument includes a base and a shaft extending distally from the base along a longitudinal axis. The shaft is configured to rotate relative to the base about the longitudinal axis. The surgical instrument also includes an end effector operatively coupled with the shaft. The end effector is configured to articulate relative to the shaft about an articulation joint. The end effector includes a first jaw and a second jaw configured to cooperate with the first jaw to clamp tissue. The second jaw is configured to support a stapling assembly. The surgical instrument further includes a firing assembly configured to be distally advanced through the shaft for driving distal translation of a staple actuator of the stapling assembly. The firing assembly is configured to be proximally retracted against at least one of the second jaw or the shaft to thereby apply a compression bias to the shaft.

20 Claims, 15 Drawing Sheets

(56)                References Cited

U.S. PATENT DOCUMENTS

| | | | |
|---|---|---|---|
| 10,245,030 | B2 | 4/2019 | Hunter et al. |
| 10,303,641 | B2 | 5/2019 | Collins et al. |
| 10,335,147 | B2 | 7/2019 | Rector et al. |
| 10,492,785 | B2 | 12/2019 | Overmyer et al. |
| 10,863,988 | B2 | 12/2020 | Patel et al. |
| 10,881,403 | B2 | 1/2021 | Shelton, IV et al. |
| 10,959,726 | B2 | 3/2021 | Williams et al. |
| 11,147,552 | B2 | 10/2021 | Burbank et al. |
| 11,234,698 | B2 | 2/2022 | Shelton, IV et al. |
| 11,311,293 | B2 | 4/2022 | Roberts et al. |
| 11,439,390 | B2 | 9/2022 | Patel et al. |
| 11,452,524 | B2 | 9/2022 | Chavan et al. |
| 11,504,124 | B2 | 11/2022 | Patel et al. |
| 11,529,140 | B2 | 12/2022 | Shelton, IV et al. |
| 11,589,865 | B2 | 2/2023 | Shelton, IV et al. |
| 11,678,877 | B2 * | 6/2023 | Shelton, IV ......... A61B 17/068 227/180.1 |
| 11,717,287 | B2 | 8/2023 | Williams et al. |
| 2005/0263562 | A1 * | 12/2005 | Shelton ............ A61B 17/07207 227/176.1 |
| 2012/0199631 | A1 * | 8/2012 | Shelton, IV ......... A61B 17/068 227/176.1 |
| 2019/0059888 | A1 | 2/2019 | Shelton, IV et al. |
| 2019/0059891 | A1 * | 2/2019 | Shelton, IV ..... A61B 17/07207 |
| 2021/0038221 | A1 * | 2/2021 | Park ...................... A61B 90/06 |
| 2022/0071726 | A1 | 3/2022 | Rockrohr et al. |

OTHER PUBLICATIONS

U.S. Appl. No. 63/634,201, entitled "Stapling and Cutting Systems for Robotic Surgery," filed Apr. 15, 2024.

* cited by examiner

300

301 — RETRACT KNIFE TO HARDSTOP

302 — APPLY SET BIASING LOAD

303 — MAINTAIN TENSION

304 — CLAMP TISSUE

305 — FIRE KNIFE / STAPLES

400

```
                        ┌─────────────────────┐
              401 ──────│  RETRACT KNIFE TO   │◀──────────────────┐
                        │      HARDSTOP       │                   │
                        └──────────┬──────────┘                   │
                                   │                              │
                        ┌──────────▼──────────┐                   │
              402 ──────│  APPLY SET CONTACT  │                   │
                        │        LOAD         │                   │
                        └──────────┬──────────┘                   │
                                   │                              │
                        ┌──────────▼──────────┐                   │
              403 ──────│   MAINTAIN TORQUE   │                   │
                        └──────────┬──────────┘                   │
                                   │                              │
          ┌────────────┌──────────▼──────────┐                   │
          │            │    TRACK MOTOR      │── 404             │
          │            │      POSITION       │                   │
          │            └─────────────────────┘                   │
          │       405         408             411                │
          │  ┌──────────┐ ┌──────────┐ ┌──────────────┐          │
          │  │ARTICULATE│ │OPEN/CLOSE│ │CLAMP TISSUE  │          │
          │  │   END    │ │   END    │ │              │          │
          │  │ EFFECTOR │ │ EFFECTOR │ │              │          │
          │  └────┬─────┘ └────┬─────┘ └──────┬───────┘          │
          │   406         409           412                      │
          │  ┌────▼─────┐ ┌────▼─────┐ ┌──────▼───────┐          │
          │  │MEASURE   │ │MEASURE   │ │ MEASURE PCR  │          │
          │  │PCR SHIFT/│ │PCR SHIFT/│ │   STRETCH    │          │
          │  │ STRETCH  │ │ STRETCH  │ │              │          │
          │  └────┬─────┘ └────┬─────┘ └──────┬───────┘          │
          │   407         410           413                      │
          │  ┌────▼─────┐ ┌────▼─────┐ ┌──────▼───────┐          │
          │  │ ADJUST   │ │ ADJUST   │ │ESTIMATE      │          │
          │  │ARTICULA- │ │ARTICULA- │ │TISSUE        │          │
          │  │  TION    │ │  TION    │ │THICKNESS     │          │
          │  └────┬─────┘ └────┬─────┘ └──────┬───────┘          │
          │       │            │         414                     │
          └───────┴────────────┘       ┌──────▼───────┐          │
                                       │MODIFY FIRING │          │
                                       │ PARAMETERS   │          │
                                       └──────┬───────┘          │
                                          415                    │
                                       ┌──────▼───────┐          │
                                       │ FIRE KNIFE / │          │
                                       │   STAPLES    │──────────┘
                                       └──────────────┘
```

FIG. 12

SURGICAL STAPLER HAVING CONTROLLABLE SHAFT BIAS

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically assisted surgery. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletal gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

In some instances, a surgical stapler may include an articulatable end effector to allow the end effector to articulate relative to a shaft of the end effector about an articulation joint, and thereby access target tissue that might otherwise be difficult to reach. However, due to the mechanical backlash that may be present within the shaft, the precise location of the articulation joint (e.g., relative to a proximal housing of the stapler) can shift as the components that define the articulation joint become biased in different directions (e.g., tension and compression), which may occur during clamping of the end effector onto layers of tissue, and/or during firing of the end effector, for example. Such shifting of the location of the articulation joint can further result in unwanted and/or unpredictable movement, such as during articulation of the end effector. The robotic surgical systems and instruments of the present disclosure seek to reduce, eliminate, or otherwise control the mechanical backlash within the shaft.

While several robotic surgical systems, instruments, and associated components have been made and used, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 12 depicts a flowchart of an example of a method for compensating for unintended movement within the surgical instrument of FIG. 8.

Figure 1:
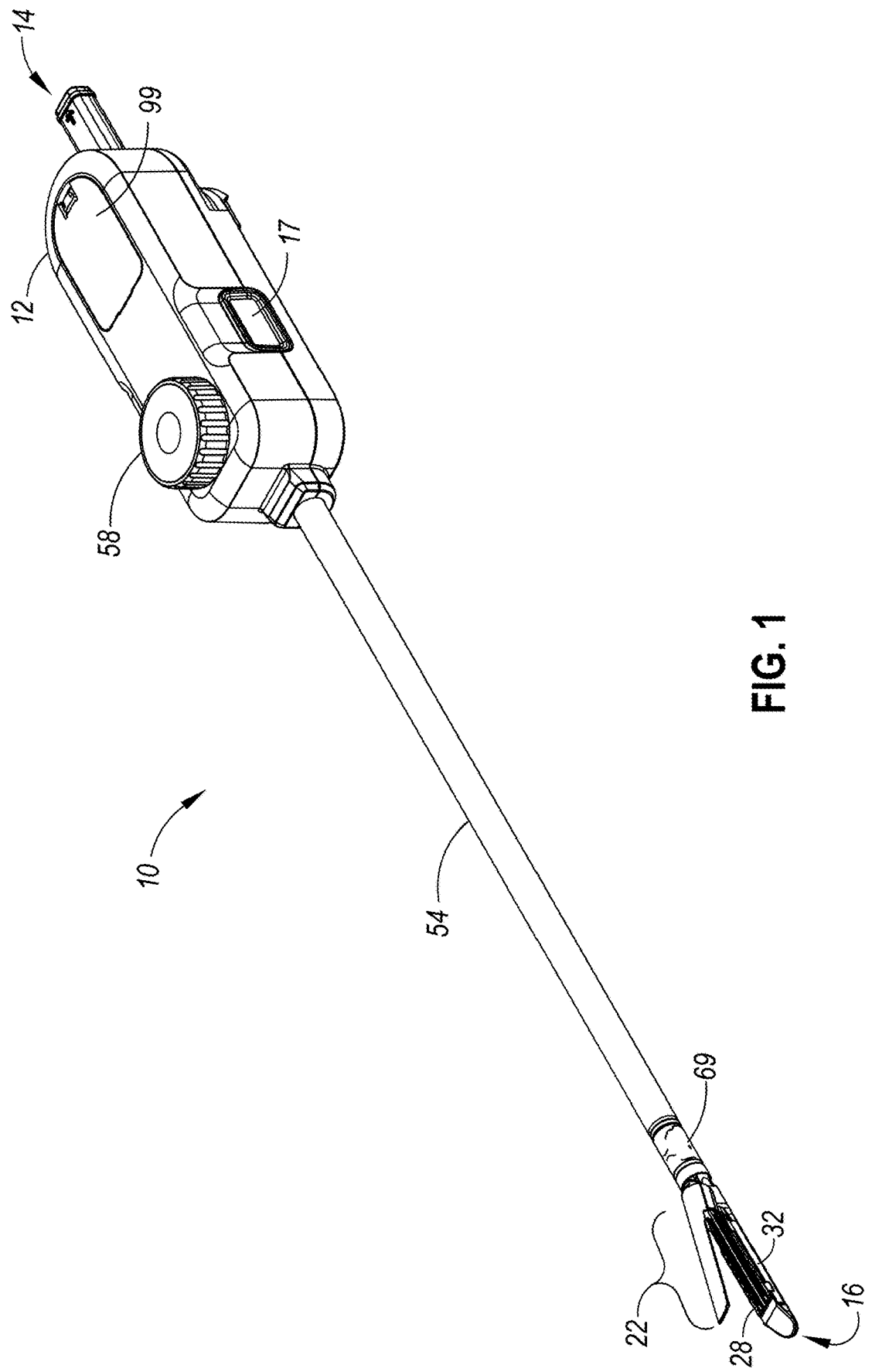
FIG. 1 depicts a perspective view of an example of a surgical instrument.
Figure 2:
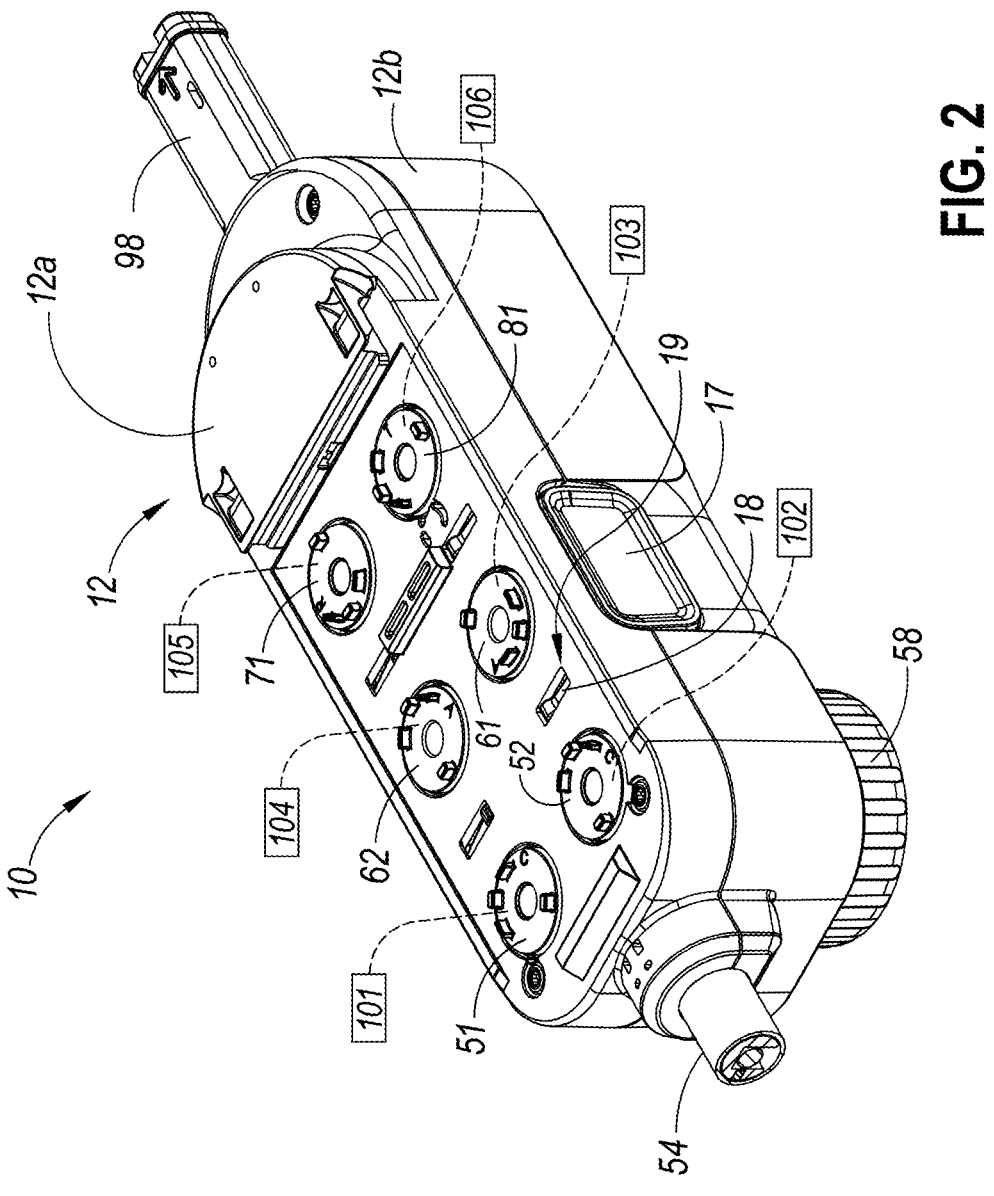
FIG. 2 depicts a perspective view of a housing of the surgical instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

Furthermore, the terms "about," "approximately," "substantially," and the like as used herein in connection with any numerical values, ranges of values, and/or geometric/positional quantifications are intended to encompass the exact value(s) referenced as well as a suitable tolerance that enables the referenced feature or combination of features to function for the intended purpose described herein. For example, "substantially parallel" encompasses nominally parallel structures.

I. Overview of Surgical Stapler

FIGS. 1-6C depict an example of a surgical instrument (10). In the example shown, surgical instrument (10) includes a housing (also referred to as a base) (12) (including a first portion (12*a*) and a second portion (12*b*)) that can be attachable to a robotic arm (100) (see FIG. 7) that includes a plurality of outputs, or rotatable disks, that can actuate pucks, or other disks, on surgical instrument (10). A proximal end (14) of surgical instrument (10) is therefore attachable to a multi-use robot (not shown), and a distal end (16) of surgical instrument (10) effects the transection and stapling of patient tissue. As shown, surgical instrument (10) includes a release button (17) that allows surgical instrument (10) to be detached from robotic arm (100). One or more de-latching bodies (18) may aid in removing surgical instrument (10) from robotic arm (100) and/or from a sterile attachment that connects surgical instrument (10) to robotic arm (100). De-latching bodies (18) can be positioned within de-latch openings (19) that enable housing (12) to be connected to robotic arm (100).

Figure 3A:
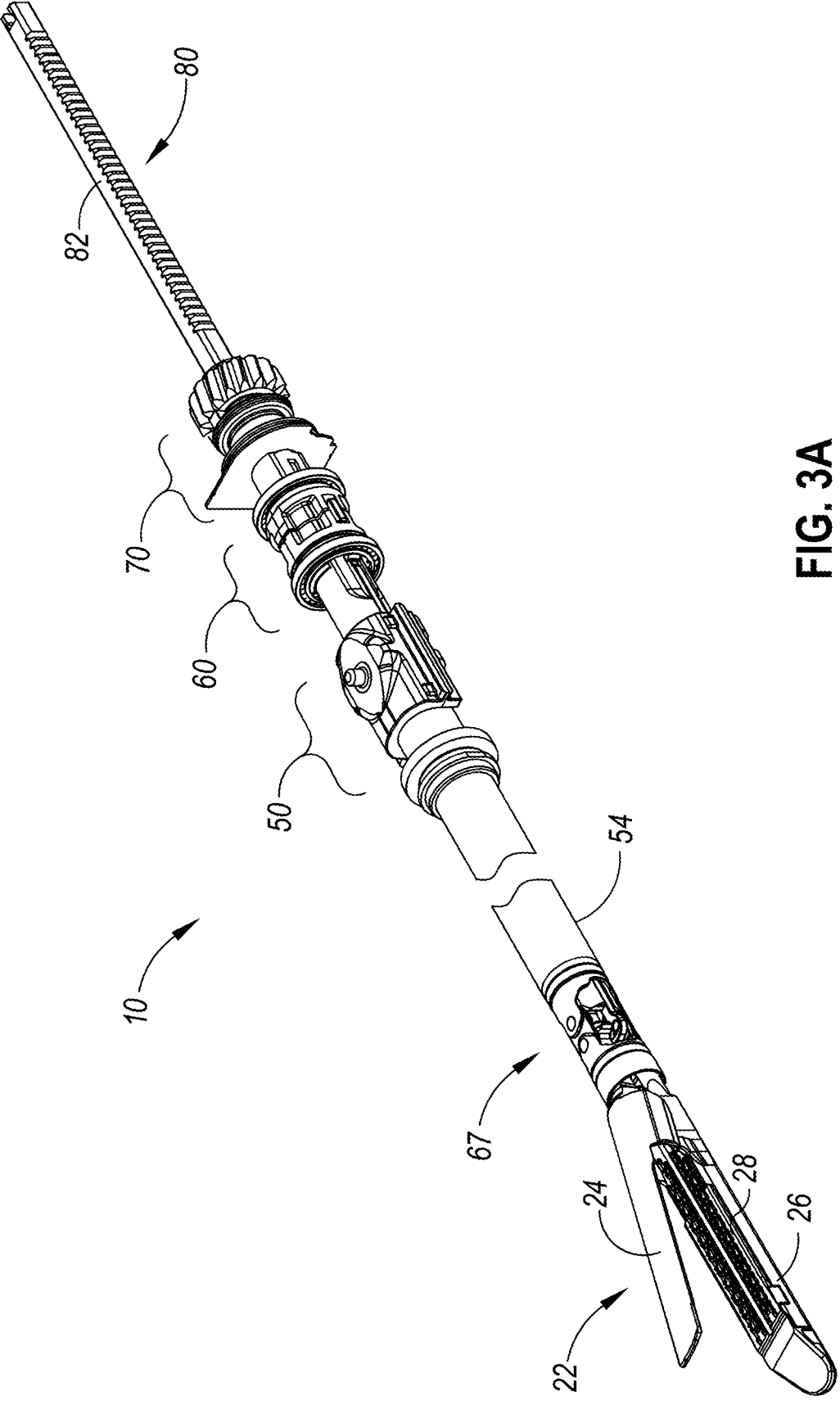
FIG. 3A depicts a perspective view of various subsystems of the surgical instrument of FIG. 1, showing an end effector of the surgical instrument in an open, non-articulated state.
Figure 3B:
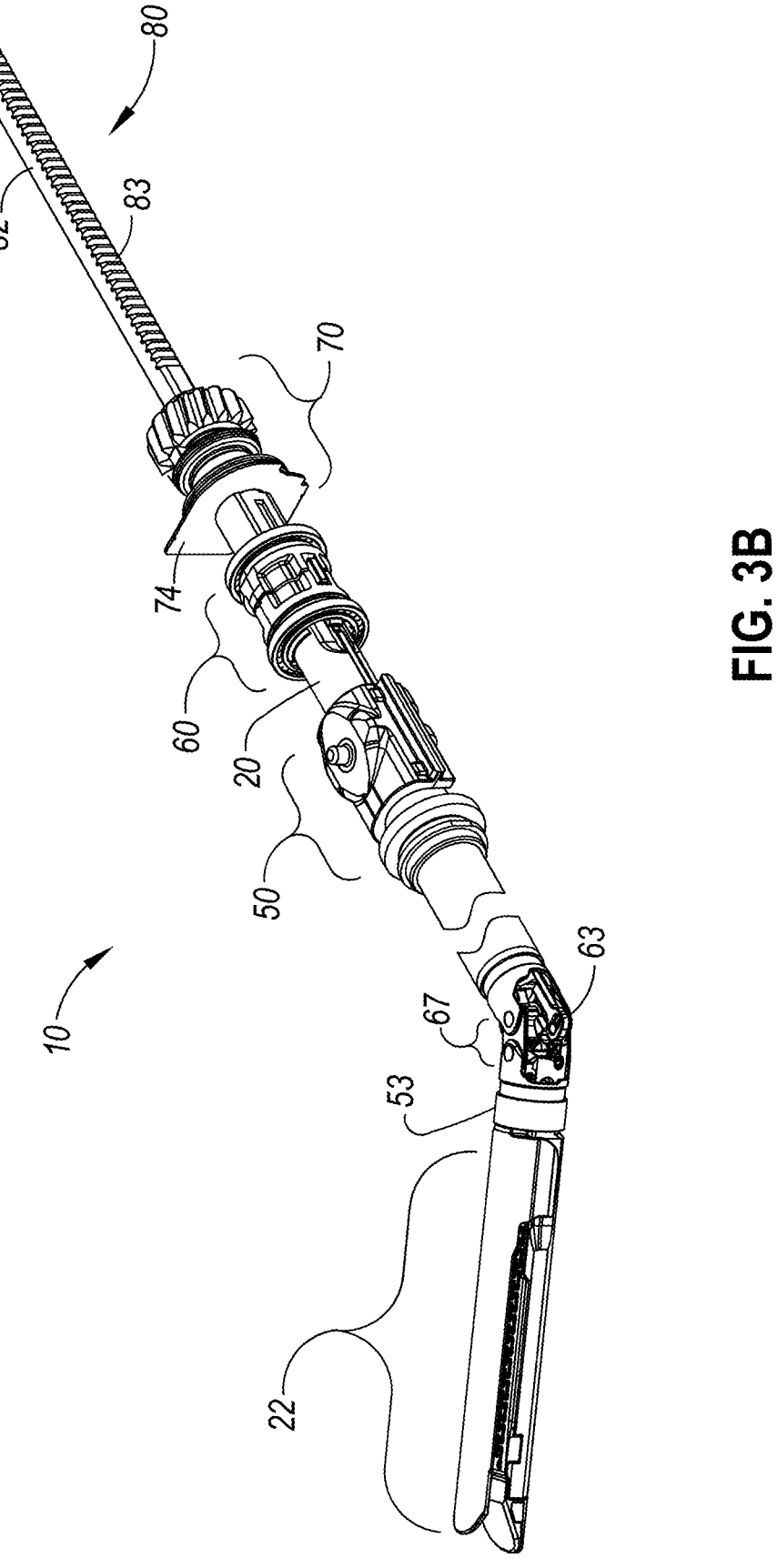
FIG. 3B depicts a perspective view of various subsystems of the surgical instrument of FIG. 1, showing the end effector of the surgical instrument in a closed, articulated state.
Figure 4:
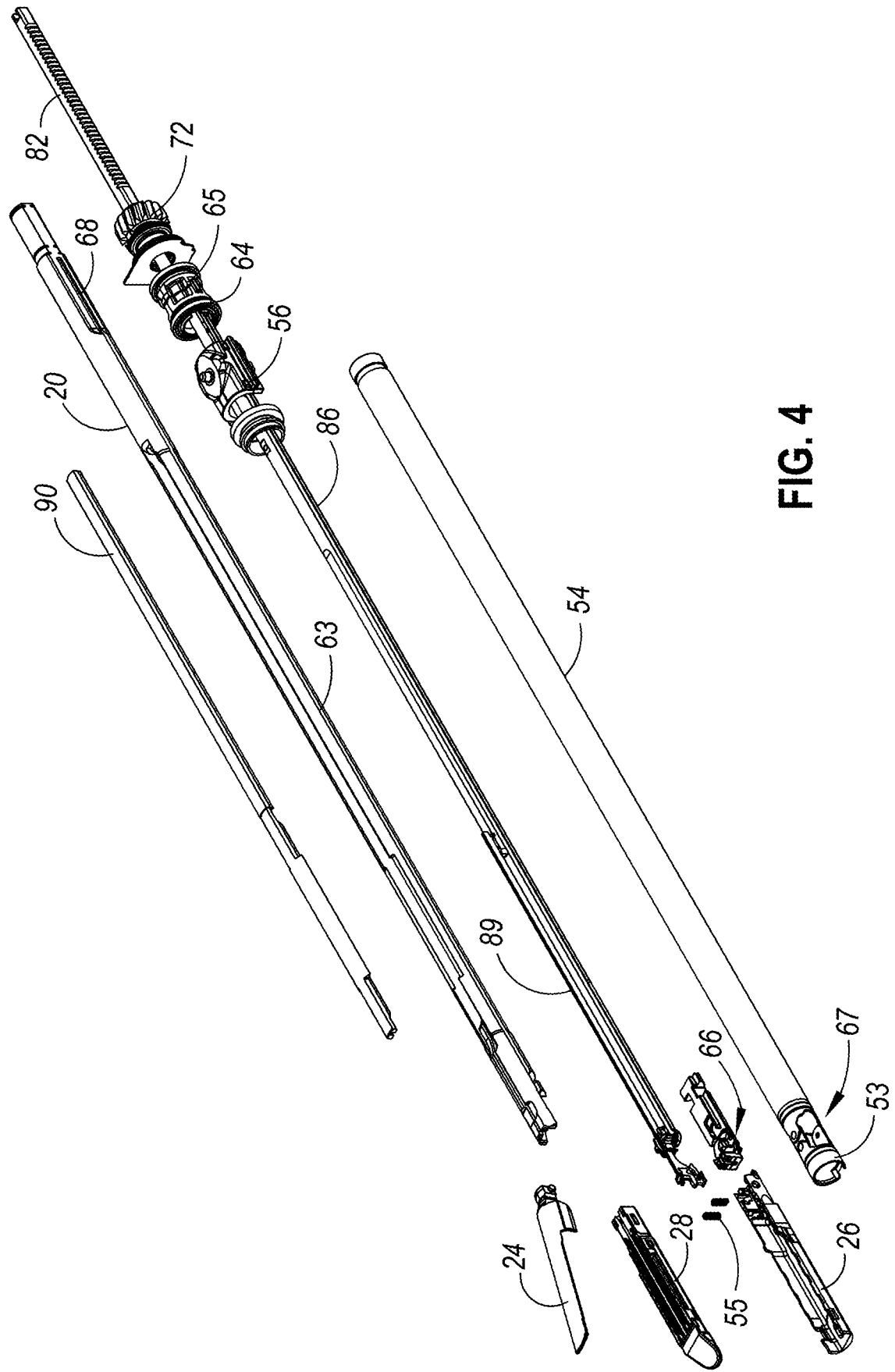
FIG. 4 depicts an exploded perspective view of various subsystems of the surgical instrument of FIG. 1.
Figure 6A:
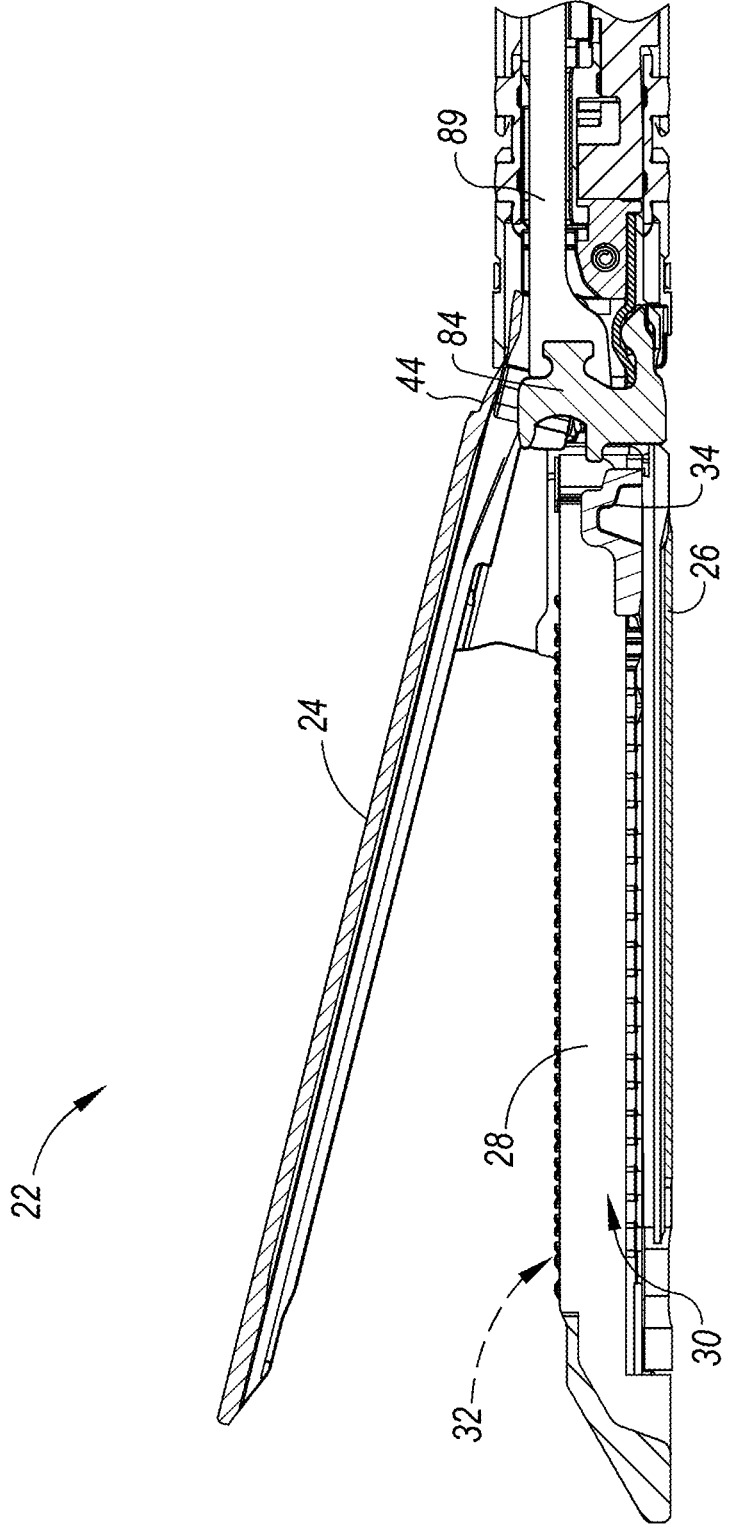
FIG. 6A depicts a cross-sectional view of the end effector of the surgical instrument of FIG. 1, showing the end effector in an open, unfired state.
Figure 6B:
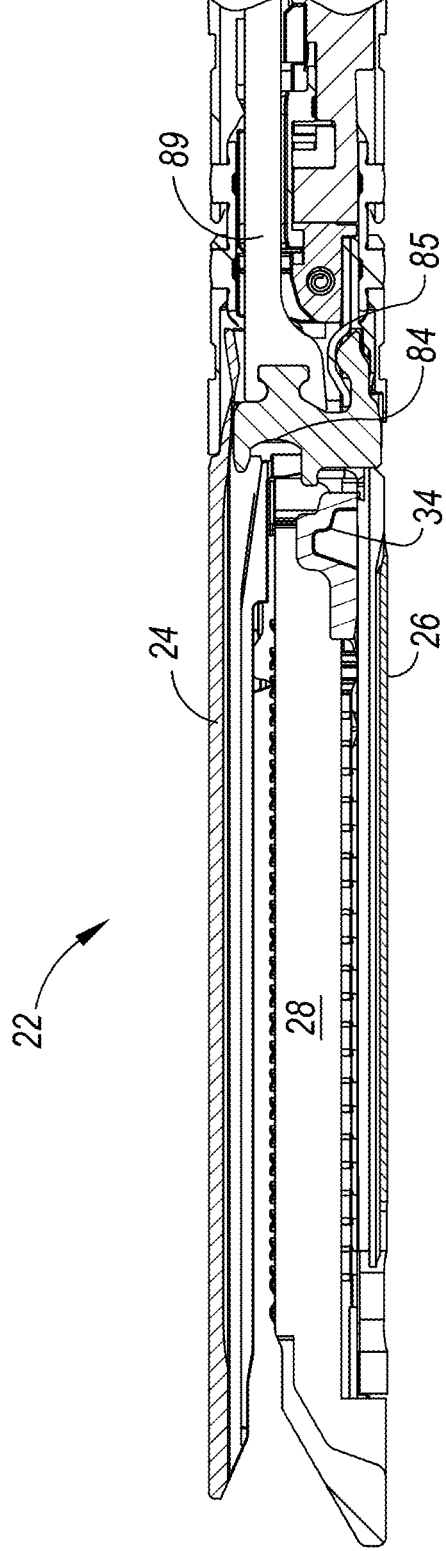
FIG. 6B depicts a cross-sectional view of the end effector of the surgical instrument of FIG. 1, showing the end effector in a closed, unfired state.
Figure 6C:
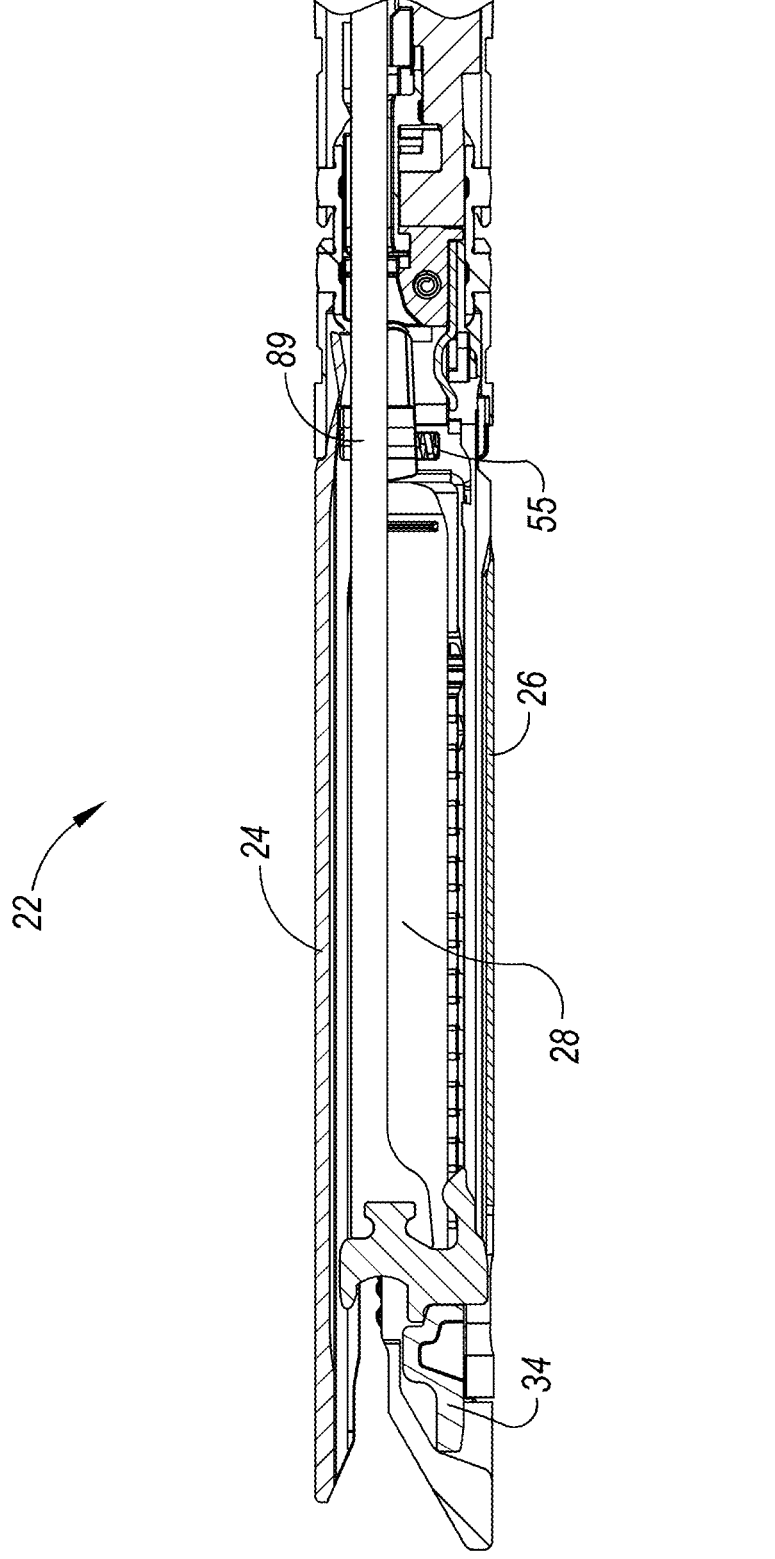
FIG. 6C depicts a cross-sectional view of the end effector of the surgical instrument of FIG. 1, showing the end effector in a closed, fired state.

As shown, surgical instrument (10) includes a rotatable shaft (also referred to as a proximal channel retainer or PCR) (20) (see FIG. 4) extending distally relative to housing (12), and an end effector (22) (see FIG. 1) coupled to shaft (20) at distal end (16). End effector (22) can be configured for cutting and stapling of tissue of a patient. As shown in FIGS. 3A-4, end effector (22) includes an anvil (also referred to as a first jaw) (24) that is rotatably connected to a lower channel (also referred to as a second jaw) (26) via a hinge (not shown). Lower channel (26) can accept a staple cartridge (also referred to as a stapling assembly) (28) within a cartridge slot (30) therein. Staple cartridge (28) includes a plurality of staples (32). A sled (also referred to as a staple actuator) (34) can be driven distally through cartridge (28) to drive staples (32) into anvil (24). Anvil (24) includes an anvil ramp (44) to facilitate closure of anvil (24) relative to lower channel (26). FIGS. 6B and 6C further illustrate end effector (22) in a closed configuration while FIG. 6A illustrates end effector (22) in an open configuration.

In this regard, surgical instrument (10) includes a closure subsystem (50), including first and second closure input pucks (51, 52) and a closure ring (53) that can be slid proximally and distally by a closure tube (54) to open and close anvil (24). Closure subsystem (50) can close anvil (24) by moving closure ring (53) distally and over anvil ramp (44), thereby hinging anvil (24) closed. As closure ring (53) is slid proximally, closure ring (53) slides away from anvil (24), allowing anvil (24) to open. Anvil (24) can be biased in an open configuration (see FIG. 6A) with a series of springs (55) (see FIG. 6C) within end effector (22). Closure tube (54) can be actuated by movement of a closure yoke (56) between an open position in which anvil (24) is opened and a closed position in which anvil (24) is closed. Closure yoke (56) can slide axially in a proximal direction to open anvil (24) and slide axially in a distal direction to cause anvil (24) to close. Closure subsystem (50) can utilize first closure input puck (51) and second closure input puck (52) for moving closure yoke (56) between the opened and closed positions. For example, first and second closure input pucks (51, 52) may each be configured to engage with a respective rotating feature of robotic arm (100), such as first and second closure robotic outputs (101, 102); and can be further coupled to respective closure input rods (not shown) that extend into housing (12) and that are operatively coupled to closure yoke (56), such as via corresponding gears (not shown), for moving closure yoke (56) between the opened and closed positions. Closure subsystem (50) can further include a manual closure spur gear (not shown) that is coupled to a manual closure knob (58) that extends through housing (12). Manual closure knob (58) provides surgical staff with the ability to open and close anvil (24) when surgical instrument (10) is disconnected from a surgical robot or to override the opening or closing of anvil (24) when connected to the surgical robot.

Surgical instrument (10) of the present example also includes an articulation subsystem (60), including first and second articulation input pucks (61, 62) and an articulation rod (63). A proximal end of articulation rod (63) can include an attachment that constrains articulation rod (63) proximally (e.g., to a first articulation bushing (64) and a second articulation bushing (65)). A distal end of articulation rod (63) can be connected to a distal channel retainer (66) that can pivot back and forth (e.g., left and right) to move, or articulate, end effector (22) of surgical instrument (10). An attachment end of distal channel retainer (66) can, for example, be attached to channel (26) of end effector (22) to articulate end effector (22). Articulation rod (63) can articulate distal channel retainer (66) back and forth about an articulation joint (67) by pushing and pulling one side of distal channel retainer (66). Articulation rod (63) moves only axially and is constrained to shaft (20) within a rod groove (68) along the length of shaft (20). Articulation subsystem (60) can utilize first articulation input puck (61) and second articulation input puck (62) for moving articulation rod (63) axially. For example, first and second articulation input pucks (61, 62) may each be configured to engage with a respective rotating feature of robotic arm (100), such as first and second articulation robotic outputs (103, 104); and can be further coupled to respective racks (not shown), such as via corresponding series of gearing (not shown), that are operable to translate proximally and distally to move first and second articulation bushings (64, 65), respectively, and thereby translate articulation rod (63) proximally and distally to pivot distal channel retainer (66) such that end effector (22) pivots between an unarticulated (e.g., straight) configuration (see FIG. 3A) and one or more articulated configurations (see FIG. 3B). Joint (67) can be concealed by a flexible sheath (69) to alleviate pinch points.

Surgical instrument (10) of the present example further includes a roll subsystem (70), including a roll input puck (71) and a series of gears that allow shaft (20) to rotate about the longitudinal axis of shaft (20). Roll subsystem (70) can utilize roll input puck (71) for rotating shaft (20). For example, roll input puck (71) may be configured to engage with a respective rotating feature of robotic arm (100), such as roll robotic output (105); and can be further coupled with a worm follower (72), such as via a worm gear (not shown), that can be operable to rotate shaft (20). To keep the worm follower (72) positioned at the correct location relative to the worm gear, roll subsystem (70) can include a stabilization plate (74) that surrounds shaft (20) distal to worm follower (72), and that can be positioned within a corresponding slot within housing (12) to prevent stabilization plate (74) from sliding axially along shaft (20), while also providing shaft (20) lateral alignment within housing (12). It will be appreciated that the rolling of shaft (20) enables end effector (22) to roll the articulation plane defined by joint (67) to any orthogonal position.

Figure 5:
FIG. 5 depicts a perspective view of the transection subsystem of the surgical instrument of FIG. 1.

Surgical instrument (10) of the present example also includes a transection subsystem (80), including a transection input puck (81) and a series of gears proximally that allow a firing rack (82) with teeth (83) to be fired distally to drive distal translation of a knife (84) for cutting tissue. Sled (34) can be pushed distally via knife (84), such that knife (84) can act both as a firing member to push sled (34) distally and as a transection member to cut tissue. Knife (84) can be retained at a closed non-fired "home" position (see FIG. 6B) by a leaf spring (85). Transection subsystem (80) can utilize transection input puck (81) for allowing firing rack (82) to be fired distally. For example, transection input puck (81) may be configured to engage with a respective rotating feature of robotic arm (100), such as transection robotic output (106); and can be further coupled with a transection drive shaft (not shown) operable to cause, either directly or indirectly via gearing, distal translation of firing rack (82), which results in firing of staples (32) and/or knife (84) in end effector (22) (see FIG. 6C). Transection subsystem (80) can include a firing gear (not shown) that is rotationally dependent on the rotation of transection input puck (81) and that is engaged with teeth (83) of firing rack (82), such that rotation of the firing gear causes a distal translation of firing rack (82). As shown in FIG. 5, transection subsystem (80) includes a firing rod (86) rotatably coupled to the distal end of firing rack (82), such that firing rod (86) can rotate independent of the firing rack (82). The rotatable connector between firing rod (86) and firing rack (82) can include a T-shaped tab (87) on a proximal end of firing rod (86) that engages with a slot (88) on firing rack (82). The tab/slot connection allows free rotation of firing rod (86) but also constrains firing rod (86) to firing rack (82) axially. The distal end of firing rod (86) can be coupled to a series of bands (89) that extend distally to knife (84) and that provide a degree of flexibility to transection subsystem (80), while also providing axial stiffness to push knife (84) through tissue. Surgical instrument (10) can include a knife insert retainer (90) that protects bands (89). In some examples, firing rack (82) can extend proximally from housing (12) and can be covered by a firing rack closure (98). In some examples, transection subsystem (80) can include a key receiver (not shown) that is rotationally coupled to the gearing of transection subsystem (80) to manually retract firing rack (82) and thus knife (84), and outer housing (12) can have a compartment (not shown) that is closed by a cover (99) that provides access to the key receiver.

Figure 7:
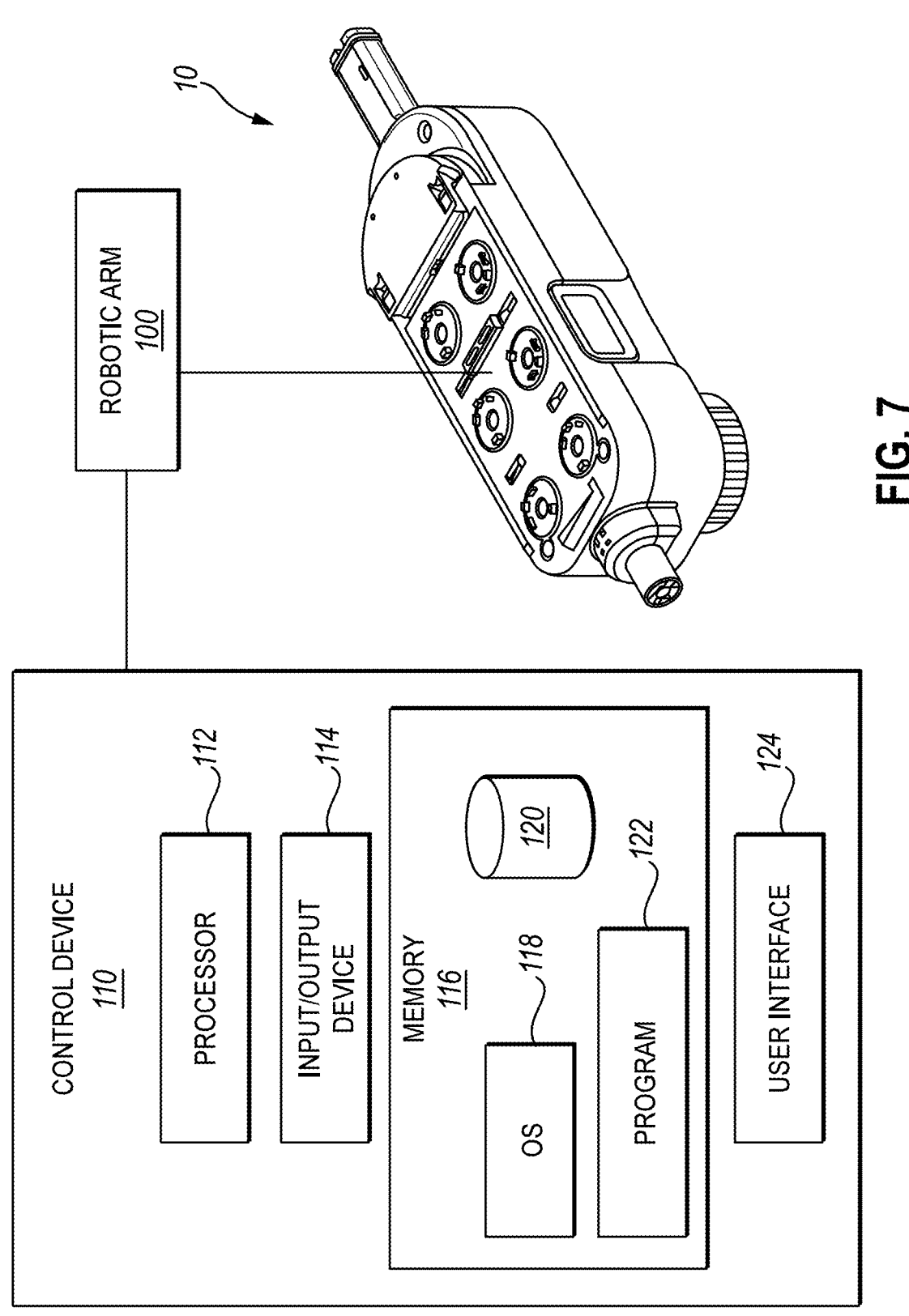
FIG. 7 depicts a block diagram of an example of a control device, an example of a robotic arm, and the surgical instrument of FIG. 1.

FIG. 7 shows an example of a control device (110) for controlling robotic arm (100) and surgical device (10). As shown, control device (110) includes a processor (112); an input/output device (114); and a memory (116) containing an operating system (OS) (118), a storage device (120), which can be any suitable repository of data, and a program (122). Input/output device (114) can be configured to receive and to output commands to control robotic arm (100) and surgical device (10). Control device (110) can include a user interface (U/I) (124) for receiving user input data (e.g., from a physician, technician, etc.), such as data representative of a click, a scroll, a tap, a press, movement of a control lever, or typing on an input device that can detect tactile inputs. Control device (110) can include a display (not shown). Memory (116) of control device (110) can include one or more memory devices that store data and instructions used to perform one or more of the methods and features disclosed herein.

By way of further example, surgical instrument (10), robotic arm (100), and/or control device (110) may be configured and operable in accordance with at least some of the teachings of U.S. App. No. 63/634,201, entitled "Stapling and Cutting Systems for Robotic Surgery," filed Apr. 15, 2024, the disclosure of which is incorporated by reference herein, in its entirety. In addition, or alternatively, surgical instrument (10), robotic arm (100), and/or control device (110) may be configured and operable in accordance with at least some of the teachings of U.S. App. No. 63/634,171, entitled "Robotic Stapling and Cutting Systems," filed Apr. 15, 2024, the disclosure of which is incorporated by reference herein, in its entirety.

II. Example of Surgical Stapler with Hard-Stop Mechanism

In some instances, it may be desirable to provide a hard stop for proximal retraction of a portion of transection subsystem (80), such as knife (84) or firing rod (86), relative to end effector (22) and/or shaft (20). For example, such a hard stop may allow any biasing within shaft (20) to be controlled, to thereby reduce, eliminate, or otherwise control the mechanical backlash within shaft (20) and thus improve control and/or predictability of the precise location of articulation joint (67) (e.g., relative to housing (12)).

Figure 8:
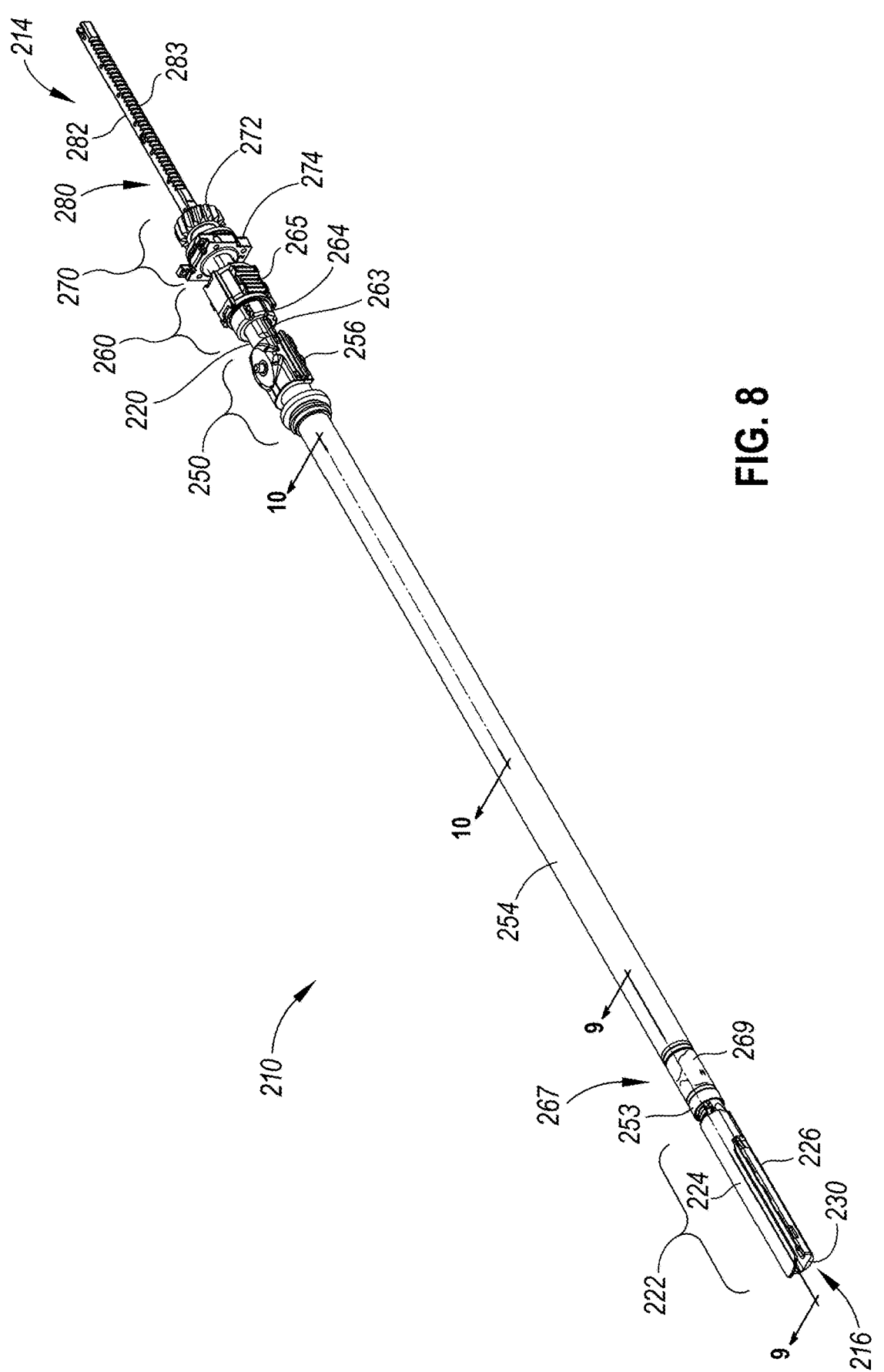
FIG. 8 depicts a perspective view of another example of a surgical instrument.
Figure 9:
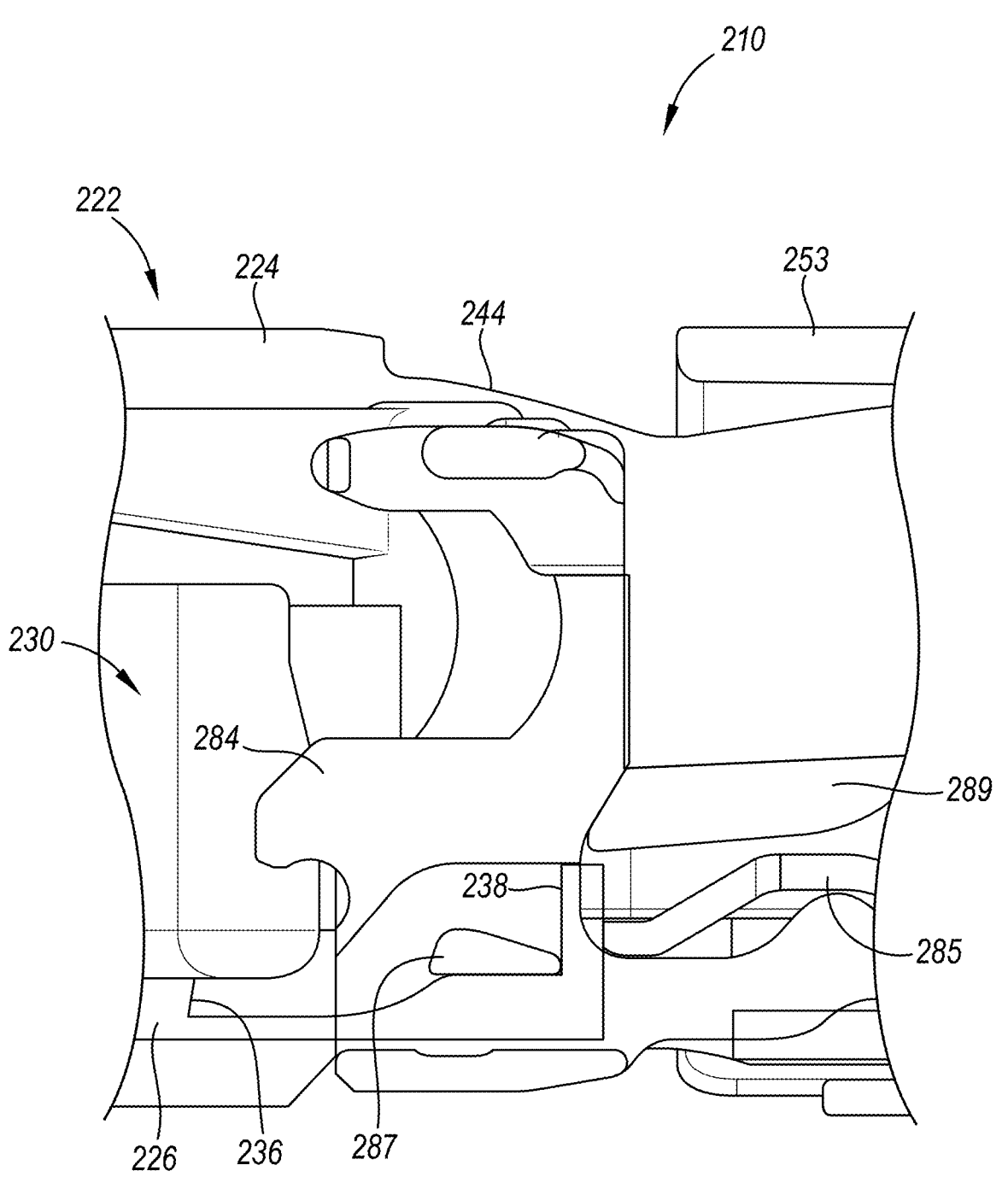
FIG. 9 depicts a cross-sectional view of the surgical instrument of FIG. 8, taken along line 9-9 in FIG. 8, showing a first hard-stop mechanism.
Figure 10:
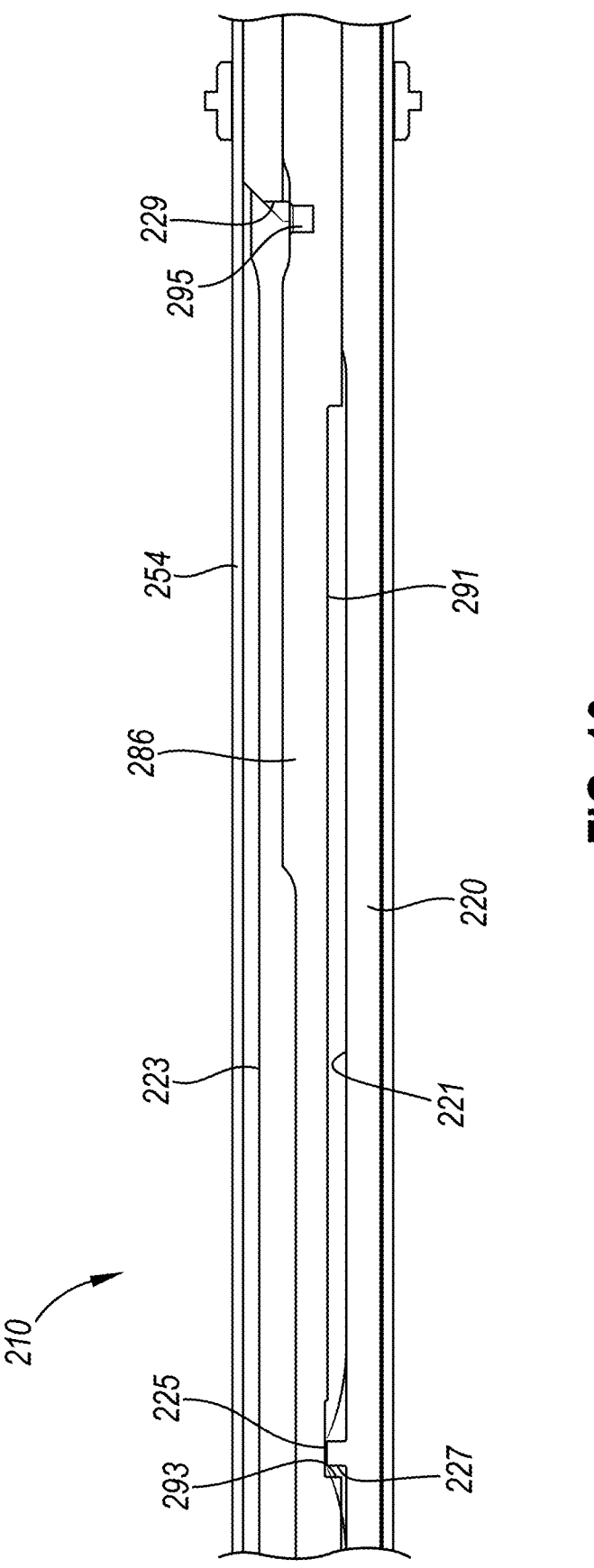
FIG. 10 depicts a cross-sectional view of the surgical instrument of FIG. 8, taken along line 10-10 in FIG. 8, showing second and third hard-stop mechanisms.

FIGS. 8-10 show a portion of an example of a surgical instrument (210) that may provide such functionality. Surgical instrument (210) may be similar to surgical instrument (10) described above, except as otherwise described below. In this regard, surgical instrument (210) may be readily incorporated into a robotic medical system in place of surgical instrument (10). Surgical instrument (210) of the present example has a proximal end (214) that is attachable to robotic arm (100), and a distal end (216) that effects the transection and stapling of patient tissue. As shown, surgical instrument (210) includes a rotatable shaft (also referred to as a proximal channel retainer or PCR) (220) extending distally relative to proximal end (214). While not shown, surgical instrument (210) may include a housing, such as housing (12) described above, at proximal end (214). As shown in FIG. 10, shaft (220) includes a shaft lumen (221) extending therethrough, and an upper longitudinal slot (223) in communication with shaft lumen (221). In the example shown, a protrusion (225) extends upwardly from a lower surface of shaft lumen (221). Protrusion (225) may define a distally-facing hard-stop wall (227), and/or a proximal end of longitudinal slot (223) may define a distally-facing hard-stop wall (229), the purposes of which are described below.

Surgical instrument (210) of the present example also includes an end effector (222) coupled to shaft (220) at distal end (216). End effector (222) can be configured for cutting and stapling of tissue of a patient. As shown in FIG. 8, end effector (222) includes an anvil (also referred to as a first jaw) (224) that is rotatably connected to a lower channel (also referred to as a second jaw) (226) via a hinge (not shown). Lower channel (226) can accept a stapling assembly (not shown), such as staple cartridge (28), within a cartridge slot (230) therein. As shown in FIG. 9, lower channel (226) includes at least one proximally-facing lockout wall (236) and at least one distally-facing hard-stop wall (238), the purposes of which are described below. Anvil (224) includes an anvil ramp (244) to facilitate closure of anvil (224) relative to lower channel (226) in a manner similar to that described above.

Surgical instrument (210) of the present example also includes a closure subsystem (250). While not shown, closure subsystem (250) may include first and second closure input pucks, such as closure input pucks (51, 52) described above. As shown in FIG. 8, closure subsystem (250) includes a closure ring (253) that can be slid proximally and distally by a closure tube (254) to open and close anvil (224) in a manner similar to that described above in connection with closure subsystem (50). In this regard, closure tube (254) can be actuated by movement of a closure yoke (256) between an open position in which anvil (224) is opened and a closed position in which anvil (224) is closed.

Surgical instrument (210) of the present example also includes an articulation subsystem (260). While not shown, articulation subsystem (260) may include first and second articulation input pucks, such as articulation input pucks (61, 62) described above. As shown in FIG. 8, articulation subsystem (260) includes an articulation rod (263). A proximal end of articulation rod (263) can include an attachment that constrains articulation rod (263) proximally (e.g., to a single articulation bushing (264) that engages with a single inboard rack (265)). A distal end of articulation rod (263) can be connected to a distal channel retainer (not shown), such as distal channel retainer (66) described above, that can pivot back and forth (e.g., left and right) to move, or articulate, end effector (222) of surgical instrument (210). Articulation rod (263) can articulate the distal channel retainer back and forth about an articulation joint (267) by pushing and pulling one side of the distal channel retainer in a manner similar to that described above in connection with articulation subsystem (60). Joint (267) can be concealed by a flexible sheath (269) to alleviate pinch points. By way of further example, articulation subsystem (260) may be configured and operable in accordance with at least some of the teachings of U.S. App. No. 63/634,171, entitled "Robotic Stapling and Cutting Systems," filed Apr. 15, 2024, the disclosure of which is incorporated by reference herein, in its entirety.

Surgical instrument (210) of the present example further includes a roll subsystem (270). While not shown, roll subsystem (270) may include a roll input puck, such as roll input puck (71) described above. As shown in FIG. 8, roll subsystem (270) includes a worm follower (272) that can be operable to rotate shaft (20) in a manner similar to that described above in connection with roll subsystem (270). In the example shown, a thrust block (274) is positioned near the proximal end of shaft (220) so as to counteract axial forces on shaft (220) caused by distal movement of closure tube (254). Thrust block (274) may be disposed distal to worm follower (272), and may include supports that engage with a buttress (not shown) that sits within the housing and distributes loads applied to the buttress from thrust block (274) (as well as other components) to the housing.

Surgical instrument (210) of the present example also includes a transection subsystem (280). While not shown, transection subsystem (280) may include a transection input puck, such as transection input puck (81) described above. As shown in FIG. 8, transection subsystem (280) includes a firing rack (282) with teeth (283) that is operable to be fired distally to drive distal translation of a knife (284) (see FIG. 9) for cutting tissue in a manner similar to that described above in connection with transection subsystem (280). As shown in FIG. 9, knife (284) can be retained at a closed non-fired "home" position by a leaf spring (285). As shown in FIG. 10, transection subsystem (280) includes a firing rod (286) rotatably coupled to the distal end of firing rack (282), such that firing rod (286) can rotate independent of the firing rack (282) in a manner similar to that described above. The distal end of firing rod (286) is coupled to a series of bands (289), that extend distally to knife (284) and that provide a degree of flexibility to transection subsystem (280), while also providing axial stiffness to push knife (284) through tissue. Firing rack (282), knife (284), firing rod (286), and bands (289) collectively define a firing assembly of transection subsystem (280).

As shown in FIG. 9, knife (284) of the present example includes a pair of laterally-outwardly extending wings (287) (one shown). In some versions, wings (287) may each be configured to contact a corresponding lockout wall (236) on lower channel (226) to stop distal movement of knife (284) in the absence of a cartridge within cartridge slot (230) (e.g., due to a downward biasing of knife (284) by leaf spring (285)), such that wings (287) may be referred to as lockout wings (287). In the example shown, wings (287) are each configured to contact a corresponding hard-stop wall (238) on lower channel (226) to limit proximal retraction of knife (284) relative to lower channel (226). Thus, knife (284) may only be retracted proximally relative to lower channel (226) until wings (287) contact the corresponding hard-stop walls (238). Once wings (287) contact the corresponding hard-stop walls (238), further proximal retraction of knife (284) relative to lower channel (226) may be prevented by the contact between wings (287) and the corresponding hard-stop walls (238). In this manner, wings (287) and the corresponding hard-stop walls (238) may collectively define a first hard-stop mechanism for limiting proximal retraction of knife (284) relative to lower channel (226), with contact between wings (287) and the corresponding hard-stop walls (238) defining an engaged state of the first hard-stop mechanism. In some cases, knife (284) and lower channel (226) may be at least slightly proximally retracted together after the first hard-stop mechanism is engaged (e.g., via a proximally-directed force applied to hard-stop walls (238) by the corresponding wings (287)), such as to take up any mechanical backlash within shaft (220).

As shown in FIG. 10, firing rod (286) of the present example includes a lower longitudinal slot (291) having a proximally-facing distal slot end (293). In the example shown, firing rod (286) also includes an upper bore (295) that is sized and configured to receive a pin (not shown) which may protrude upwardly from upper bore (295). In some versions, distal slot end (293) of firing rod (286) may be configured to contact hard-stop wall (227) on shaft (220)

to limit proximal retraction of firing rod (286) relative to shaft (220). Thus, firing rod (286) may only be retracted proximally relative to shaft (220) until distal slot end (293) contacts hard-stop wall (227). Once distal slot end (293) contacts hard-stop wall (227), further proximal retraction of firing rod (286) relative to shaft (220) may be prevented by the contact between distal slot end (293) and hard-stop wall (227). In this manner, distal slot end (293) and hard-stop wall (227) may collectively define a second hard-stop mechanism for limiting proximal retraction of firing rod (286) relative to shaft (220), with contact between distal slot end (293) and hard-stop wall (227) defining an engaged state of the second hard-stop mechanism. In some cases, firing rod (286) and shaft (220) may be at least slightly proximally retracted together after the second hard-stop mechanism is engaged (e.g., via a proximally-directed force applied to hard-stop wall (227) by distal slot end (293)), such as to take up any mechanical backlash within shaft (220).

In some other versions, the pin received within upper bore (295) may be configured to contact hard-stop wall (229) on shaft (220) to limit proximal retraction of firing rod (286) relative to shaft (220). Thus, firing rod (286) may only be retracted proximally relative to shaft (220) until the pin received within upper bore (295) contacts hard-stop wall (229). Once the pin received within upper bore (295) contacts hard-stop wall (229), further proximal retraction of firing rod (286) relative to shaft (220) may be prevented by the contact between the pin received within upper bore (295) and hard-stop wall (229). In this manner, the pin received within upper bore (295) and hard-stop wall (229) may collectively define a third hard-stop mechanism for limiting proximal retraction of firing rod (286) relative to shaft (220), with contact between the pin received within upper bore (295) and hard-stop wall (229) defining an engaged state of the third hard-stop mechanism. In some cases, firing rod (286) and shaft (220) may be at least slightly proximally retracted together after the third hard-stop mechanism is engaged (e.g., via a proximally-directed force applied to hard-stop wall (229) by the pin received within upper bore (295)), such as to take up any mechanical backlash within shaft (220).

While first, second, and third hard-stop mechanisms for limiting proximal retraction of knife (284) and/or firing rod (286) have been described, it will be appreciated that only one hard-stop mechanism may be sufficient to limit proximal retraction of knife (284) and/or firing rod (286). For example, in instances where the hard stop is provided by the contact between wings (287) and the corresponding hard-stop walls (238), any one or more of hard-stop walls (227, 229), distal slot end (293), and/or the pin received within upper bore (295) may be omitted. Similarly, in instances where the hard stop is provided by the contact between distal slot end (293) and hard-stop wall (227), any one or more of hard-stop walls (229, 238), wings (287), and/or the pin received within upper bore (295) may be omitted. In some instances where the hard stop is provided by the contact between distal slot end (293) and hard-stop wall (227) or where the hard stop is provided by the contact between the pin received within upper bore (295) and hard-stop wall (229), wings (287) and the corresponding hard-stop walls (238) may still be present; in such cases, wings (287) may be spaced apart from the corresponding hard-stop walls (238) by corresponding gaps when distal slot end (293) contacts hard-stop wall (227), or when the pin received within upper bore (295) contacts hard-stop wall (229).

In some versions, transection subsystem (280) may be configured to apply one or more predetermined forces to shaft (220) via any of the first, second, or third hard-stop mechanisms. For example, transection subsystem (280) may be configured to apply a compression bias to shaft (220) via any of the first, second, or third hard-stop mechanisms. In addition, or alternatively, transection subsystem (280) may be configured to apply a minimum force to shaft (220) that is sufficient to maintain contact between the individual members of any of the first, second, or third hard-stop mechanisms. In this regard, transection robotic output (106) may be configured to rotate transection input puck (81) to proximally retract firing rack (282), and thus firing rod (286) and knife (284); and to continue to apply one or more predetermined amounts of torque to transection input puck (81) after the first, second, or third hard-stop mechanism has been engaged, to thereby place knife (284) and/or firing rod (286) in tension. Placing knife (284) and/or firing rod (286) in tension may, in turn, place shaft (220) in compression. In addition, or alternatively, placing knife (284) and/or firing rod (286) in tension may maintain engagement of the first, second, or third hard-stop mechanism. As described in greater detail below, any of the first, second, or third hard-stop mechanisms may be utilized to mitigate unintended movement within surgical instrument (210), and/or to compensate for unintended movement within surgical instrument (210).

As noted above, surgical instrument (210) may be readily incorporated into a robotic medical system in place of surgical instrument (10). Thus, control device (110) may be used for controlling robotic arm (100) and surgical device (210). In this regard, control device (110) may be configured to output commands to one or more motors (not shown) of robotic arm (100) that are each configured to drive rotation of a corresponding robotic output (101, 102, 103, 104, 105, 106) and thereby rotate the corresponding input puck (51, 52, 61, 62, 71, 81) of surgical device (210). For example, control device (110) may be configured to output commands to rotate transection robotic output (106) via a corresponding motor (not shown) of robotic arm (100) to rotate transection input puck (81) for translating firing rack (282), knife (284), and firing rod (286). Any one or more of such motors may be equipped with one or more corresponding sensors for detecting one or more parameters associated with such motor(s). For example, any one or more of such motors may be equipped with torque, force, current, or other suitable sensors, which may be in operative communication with control device (110) so that control device (110) may monitor a condition of such motor(s) based on signals received by control device (110) from such sensor(s).

III. Example of Method for Mitigating Unintended Movement

Figure 11:
FIG. 11 depicts a flowchart of an example of a method for mitigating unintended movement within the surgical instrument of FIG. 8.
Figure 11:
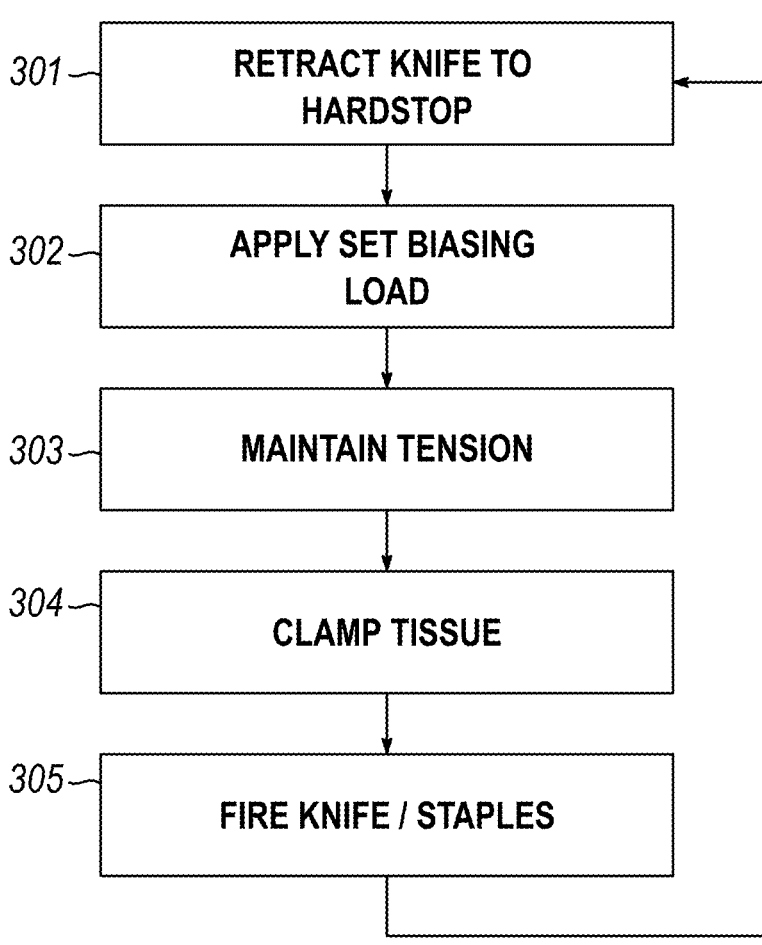

Referring now to FIG. 11, an example of a method (300) for mitigating unintended movement within surgical instrument (210) begins at step (301), at which knife (284) and/or firing rod (286) are retracted proximally to engage one of the first, second, or third hard-stop mechanisms. For example, transection robotic output (106) may be rotated by a corresponding motor of robotic arm (100) to rotate transection input puck (81) to proximally retract firing rack (282), knife (284), and firing rod (286) such that wings (287) contact the corresponding hard-stop walls (238) to engage the first hard-stop mechanism. In such cases, the proximal retraction may continue until the mechanical backlash is taken up in shaft (220). As another example, transection robotic output (106) may rotate transection input puck (81) to proximally retract firing rack (282), knife (284), and firing rod (286)

such that distal slot end (293) contacts hard-stop wall (227) to engage the second hard-stop mechanism; or such that the pin received within upper bore (295) contacts hard-stop wall (229) to engage the third hard-stop mechanism. In such cases, the proximal retraction may continue until the mechanical backlash is taken up in at least a proximal portion of shaft (220), such as the portion of shaft (220) that is proximal of the engaged hard-stop mechanism. The proximal retraction of knife (284) and/or firing rod (286) may be automatically initiated by control device (110), such as after surgical instrument (210) is attached to robotic arm (100). The engagement of any of the first, second, or third hard-stop mechanisms may be detected by control device (110) based on signals received from the torque, force, current, or other suitable sensor(s) coupled to the motor corresponding to transection robotic output (106)).

Method (300) proceeds from step (301) to step (302), at which transection robotic output (106) is rotated further to apply a predetermined unidirectional (e.g., compression) biasing load to shaft (220) that is sufficient to continuously maintain engagement of the first, second, or third hard-stop mechanism. For example, the predetermined biasing load may be sufficient to continuously maintain contact between wings (287) and the corresponding hard-stop walls (238) to continuously maintain engagement of the first hard-stop mechanism. As another example, the predetermined biasing load may be sufficient to continuously maintain contact between distal slot end (293) and hard-stop wall (227) to continuously maintain engagement of the second hard-stop mechanism. The application of the predetermined biasing load may be automatically performed by control device (110) after step (301).

Method (300) proceeds from step (302) to step (303), at which knife (284) and/or firing rod (286) is continuously maintained in tension, such as during articulation of end effector (222). For example, at least one of the following parameters may be continuously maintained: the angular position of an output shaft of the motor corresponding to transection robotic output (106) (e.g., such that transection robotic output (106) and transection input puck (81) are fixed against rotation); the torque applied by the output shaft of the motor corresponding to transection robotic output (106) (e.g., such that transection robotic output (106) and transection input puck (81) may rotate); and/or the predetermined biasing load applied to shaft (220) (e.g., by utilizing a compensation equation with other signals received from the motor corresponding to transection robotic output (106)). The continuous maintaining of knife (284) and/or firing rod (286) in tension may be automatically performed by control device (110) after step (302).

Method (300) proceeds from step (303) to step (304), at which end effector (222) clamps tissue. Method (300) proceeds from step (304) to step (305), at which end effector (222) is fired to transect the clamped tissue and/or deploy staples into the clamped tissue. During step (305), the angular position of the output shaft of the motor corresponding to transection robotic output (106) is rotated, such that transection robotic output (106) and transection input puck (81) are rotated to drive distal translation of knife (284). Thus, tension is relieved from knife (284), and the clamped tissue is transected. The clamping of tissue via end effector (222) and/or the firing of end effector (222) may be performed based on user input provided to control device (110).

In the example shown, method (300) returns from step (305) to step (301), at which knife (284) and/or firing rod (286) are again retracted proximally so that method (300) may be repeated, which may include resuming tensioning of knife (284) and/or firing rod (286). In some versions, method (300) may conclude upon completion of step (305). As noted above, various steps of method (300) may be performed by control device (110) automatically and/or based on user input provided to control device (110). For example, memory (116) of control device (110) can include one or more memory devices that store data and instructions used to perform method (300).

IV. Example of Method for Compensating for Unintended Movement

Referring now to FIG. 12, an example of a method (400) for compensating for unintended movement within surgical instrument (210) begins at step (401), at which knife (284) and/or firing rod (286) are retracted proximally to engage one of the first, second, or third hard-stop mechanisms. For example, transection robotic output (106) may be rotated by the corresponding motor of robotic arm (100) to rotate transection input puck (81) to proximally retract firing rack (282), knife (284), and firing rod (286) such that wings (287) contact the corresponding hard-stop walls (238) to engage the first hard-stop mechanism. In such cases, the proximal retraction may continue until the mechanical backlash is taken up in shaft (220). As another example, transection robotic output (106) may rotate transection input puck (81) to proximally retract firing rack (282), knife (284), and firing rod (286) such that distal slot end (293) contacts hard-stop wall (227) to engage the second hard-stop mechanism; or such that the pin received within upper bore (295) contacts hard-stop wall (229) to engage the third hard-stop mechanism. In such cases, the proximal retraction may continue until the mechanical backlash is taken up in at least a proximal portion of shaft (220), such as the portion of shaft (220) that is proximal of the engaged hard-stop mechanism. The proximal retraction of knife (284) and/or firing rod (286) may be automatically initiated by control device (110), such as after surgical instrument (210) is attached to robotic arm (100). The engagement of any of the first, second, or third hard-stop mechanisms may be detected by control device (110) based on signals received from the torque, force, current, or other suitable sensor(s) coupled to the motor corresponding to transection robotic output (106)).

Method (400) proceeds from step (401) to step (402), at which transection robotic output (106) is rotated further to apply a predetermined contact load to shaft (220) that is sufficient to continuously maintain engagement of the first, second, or third hard-stop mechanism. For example, the predetermined contact load may be sufficient to continuously maintain contact between wings (287) and the corresponding hard-stop walls (238) to continuously maintain engagement of the first hard-stop mechanism. As another example, the predetermined contact load may be sufficient to continuously maintain contact between distal slot end (293) and hard-stop wall (227) to continuously maintain engagement of the second hard-stop mechanism. The application of the predetermined contact load may be automatically performed by control device (110) after step (401).

Method (400) proceeds from step (402) to step (403), at which the torque applied by the output shaft of the motor corresponding to transection robotic output (106) is continuously maintained (e.g., such that transection robotic output (106) and transection input puck (81) may rotate). Method (400) proceeds from step (403) to step (404), at which the angular position of the output shaft of the motor corresponding to transection robotic output (106) is continuously tracked. Since the torque applied by the output shaft is continuously maintained at step (403), it will be appreciated that the angular position of the output shaft that is continuously tracked at step (404) may serve as a "follower" that may be indicative of movement, such as unintended movement within surgical instrument (210) (e.g., within shaft (220)). In some versions, step (404) and step (403) may be performed simultaneously with each other. The continuous maintaining of the torque applied by the output shaft of the motor corresponding to transection robotic output (106), and/or the continuous tracking of the angular position of the output shaft of the motor corresponding to transection robotic output (106), may be automatically performed by control device (110) after step (402).

As shown, method (400) may proceed from step (404) to step (405), at which end effector (222) is articulated. For example, end effector (222) may be articulated left or right, such that articulation rod (263) is placed in compression or tension, respectively; and the compressive or tensive load applied to articulation rod (263) may be resolved through shaft (220), thereby causing shaft (220) to be placed in tension or compression, respectively. The tensive or compressive loading on shaft (220) may cause shaft (220) to shift (e.g., through mechanical backlash) or stretch (e.g., through mechanical compliance). The articulation of end effector (222) may be performed based on user input provided to control device (110). Method (400) proceeds from step (405) to step (406), at which such shifting or stretching of shaft (220) is measured based on the angular position of the output shaft that is continuously tracked at step (404). Method (400) proceeds from step (406) to step (407), at which the articulation of end effector (222) is adjusted based on the shifting or stretching of shaft (220) measured at step (406) to compensate for the shifting or stretching of shaft (220). The continuous measuring of the shifting or stretching of shaft (220), and/or the adjusting of the articulation of end effector (222), may be automatically performed by control device (110) after (and/or during) step (405). In the example shown, method (400) returns from step (407) to step (404) for continued tracking of the angular position of the output shaft of the motor.

As shown, method (400) may additionally or alternatively proceed from step (404) to step (408), at which end effector (222) is closed or opened, such that closure tube (254) is placed in compression or tension, respectively; and the compressive or tensive load applied to closure tube (254) may be resolved through shaft (220), thereby causing shaft (220) to be placed in tension or compression, respectively. The tensive or compressive loading on shaft (220) may cause shaft (220) to shift (e.g., through mechanical backlash) or stretch (e.g., through mechanical compliance). The closing or opening of end effector (222) may be performed based on user input provided to control device (110). Method (400) proceeds from step (408) to step (409), at which such shifting or stretching of shaft (220) is measured based on the angular position of the output shaft that is continuously tracked at step (404). Method (400) proceeds from step (409) to step (410), at which the articulation of end effector (222) is adjusted based on the shifting or stretching of shaft (220) measured at step (409) to compensate for the shifting or stretching of shaft (220). The continuous measuring of the shifting or stretching of shaft (220), and/or the adjusting of the articulation of end effector (222), may be automatically performed by control device (110) after (and/or during) step (408). In the example shown, method (400) returns from step (410) to step (404) for continued tracking of the angular position of the output shaft of the motor.

As shown, method (400) may additionally or alternatively proceed from step (404) to step (411), at which end effector (222) clamps tissue. The clamping load may cause shaft (220) to stretch (e.g., through mechanical compliance). The clamping of tissue via end effector (222) may be performed based on user input provided to control device (110). Method (400) proceeds from step (411) to step (412), at which such stretching of shaft (220) is measured based on the angular position of the output shaft that is continuously tracked at step (404). Method (400) proceeds from step (412) to step (413), at which the tissue thickness is estimated based on the angular position of the output shaft that is continuously tracked at step (404). In the example shown, method (400) proceeds from step (413) to step (414), at which the firing control parameters are modified based on the tissue thickness estimated at step (413). For example, such firing control parameters may include a desired torque to be applied by the output shaft of the motor corresponding to transection robotic output (106) that is sufficient for transecting tissue having the thickness estimated at step (413). The measuring of the stretching of shaft (220), the estimating of the tissue thickness, and/or the modifying of the firing control parameters, may be automatically performed by control device (110) after (and/or during) step (411). Method (400) proceeds from step (414) to step (415), at which end effector (222) is fired to transect the clamped tissue and/or deploy staples into the clamped tissue, such as by using the firing control parameters modified at step (414). The firing of end effector (222) may be performed based on user input provided to control device (110). In some versions, step (414) may be omitted, such as in instances where the estimated tissue thickness may not warrant modifying the firing control parameters, such that method (400) may proceed directly from step (413) to step (415).

In the example shown, method (400) returns from step (415) to step (401), at which knife (284) and/or firing rod (286) are again retracted proximally so that method (400) may be repeated, which may include resuming tensioning of knife (284) and/or firing rod (286). In some versions, method (400) may conclude upon completion of step (415). As noted above, various steps of method (400) may be performed by control device (110) automatically and/or based on user input provided to control device (110). For example, memory (116) of control device (110) can include one or more memory devices that store data and instructions used to perform method (400). In some cases, control device (110) may be configured to integrate various steps of method (300) into method (400). For example, control device (110) may be configured to execute various steps of method (300) for mitigating unintended movement within surgical instrument (210), and to then execute various steps of method (400) for compensating for any unintended movement that might inadvertently occur within surgical instrument (210).

V. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument (210) comprising: (a) a base (12); (b) a shaft (220) extending distally from the base along a longitudinal axis, wherein the shaft is configured to rotate relative to the base about the longitudinal axis; (c) an end effector (222) operatively coupled with the shaft, wherein the end effector is configured to articulate relative to the shaft about an articulation joint (267), wherein the end effector includes: (i) a first jaw (224), and (ii) a second jaw (226) configured to cooperate with the first jaw to clamp tissue, wherein the second jaw is configured to support a stapling assembly (28); and (d) a firing assembly (280) configured to be distally advanced through the shaft for driving distal translation of a staple actuator (34) of the stapling assembly, wherein the firing assembly is configured to be proximally retracted against at least one of the second jaw or the shaft to thereby apply a compression bias to the shaft.

Example 2

The surgical instrument of Example 1, wherein the firing assembly is configured to be proximally retracted against the second jaw to thereby apply the compression bias to the shaft.

Example 3

The surgical instrument of Example 2 wherein the firing assembly includes a knife (284), wherein the knife is configured to be proximally retracted against the second jaw to thereby apply the compression bias to the shaft.

Example 4

The surgical instrument of Example 3, wherein the knife includes at least one laterally-outwardly extending wing (287), wherein the second jaw includes at least one distally-facing hard-stop wall (238), wherein the at least one laterally-outwardly extending wing knife is configured to be proximally retracted against the at least one distally-facing hard-stop wall to thereby apply the compression bias to the shaft.

Example 5

The surgical instrument of Example 4, wherein the at least one laterally-outwardly extending wing includes at least one lockout wing.

Example 6

The surgical instrument of Example 1, wherein the firing assembly is configured to be proximally retracted against the shaft to thereby apply the compression bias to the shaft.

Example 7

The surgical instrument of Example 6, wherein the firing assembly includes a firing rod (286), wherein the firing rod is configured to be proximally retracted against the shaft to thereby apply the compression bias to the shaft.

Example 8

The surgical instrument of Example 7, wherein the firing rod includes a proximally-facing surface (293), wherein the shaft includes a distally-facing hard-stop wall (227), wherein the proximally-facing surface is configured to be proximally retracted against the distally-facing hard-stop wall to thereby apply the compression bias to the shaft.

Example 9

The surgical instrument of Example 8, wherein the firing rod includes a longitudinal slot (291), wherein the longitudinal slot has a distal slot end defining the proximally-facing surface.

Example 10

The surgical instrument of any of Examples 8 through 9, wherein the shaft includes a protrusion (225), wherein the protrusion defines the distally-facing hard-stop wall (227).

Example 11

A robotic surgical system comprising: (a) the surgical instrument of any of Examples 1 through 10; and (b) a robotic arm (100) having at least one rotatable output (106) configured to distally advance and proximally retract the firing assembly.

Example 12

The robotic surgical system of Example 11, further comprising a control device (110) configured to instruct a motor of the robotic arm to rotate the at least one rotatable output to distally advance and proximally retract the firing assembly.

Example 13

The robotic surgical system of Example 12, wherein the control device is configured to instruct the motor of the robotic arm to rotate the at least one rotatable output to proximally retract the firing assembly against the at least one of the second jaw or the shaft to thereby apply the compression bias to the shaft.

Example 14

The robotic surgical system of Example 13, wherein the control device is configured to instruct the motor of the robotic arm to continuously maintain the firing assembly in tension prior to distally advancing the firing assembly.

Example 15

The robotic surgical system of any of Examples 13 through 14, wherein the control device is configured to instruct the motor of the robotic arm to continuously supply a predetermined torque to the surgical instrument prior to distally advancing the firing assembly.

Example 16

The robotic surgical system of Example 15, wherein the control device is configured to continuously track an angular position of an output shaft of the motor.

Example 17

The robotic surgical system of Example 16, wherein the control device is configured to measure at least one of a shifting of the shaft or a stretching of the shaft based on the angular position of the output shaft of the motor.

Example 18

The robotic surgical system of Example 17, wherein the control device is configured to adjust an articulation of the end effector based on the at least one of the shifting of the shaft or the stretching of the shaft.

Example 19

The robotic surgical system of any of Examples 16 through 18, wherein the control device is configured to estimate a thickness of the tissue based on the angular position of the output shaft of the motor.

Example 20

The robotic surgical system of Example 19, wherein the control device is configured to modify firing parameters for distally advancing the firing assembly based on the thickness of the tissue.

Example 21

A robotic surgical system comprising: (a) a surgical instrument (110) comprising: (i) a base (12), (ii) a shaft (220) extending distally from the base along a longitudinal axis, wherein the shaft is configured to rotate relative to the base about the longitudinal axis, (iii) an end effector (222) operatively coupled with the shaft, wherein the end effector is configured to articulate relative to the shaft about an articulation joint (267), wherein the end effector includes: (A) a first jaw (224), and (B) a second jaw (226) configured to cooperate with the first jaw to clamp tissue, wherein the second jaw is configured to support a stapling assembly (28), and (iv) a firing assembly (280); (b) a robotic arm (100) having at least one rotatable output (106) operatively coupled with the firing assembly; and (c) a control device (110) configured to: (i) instruct a motor of the robotic arm to rotate the at least one rotatable output in a first direction to distally advance the firing assembly through the shaft for driving distal translation of a staple actuator (34) of the stapling assembly, and (ii) instruct the motor of the robotic arm to rotate the at least one rotatable output in a second direction to proximally retract the firing assembly against at least one of the second jaw or the shaft to thereby apply a compression bias to the shaft.

Example 22

The robotic surgical system of Example 21, wherein the control device is configured to instruct the motor of the robotic arm to rotate the at least one rotatable output in the second direction to proximally retract the firing assembly against the second jaw to thereby apply the compression bias to the shaft.

Example 23

The robotic surgical system of Example 21, wherein the control device is configured to instruct the motor of the robotic arm to rotate the at least one rotatable output in the second direction to proximally retract the firing assembly against the shaft to thereby apply the compression bias to the shaft.

Example 24

The robotic surgical system of any of Examples 21 through 23, wherein the control device is configured to instruct the motor of the robotic arm to continuously maintain the firing assembly in tension prior to distally advancing the firing assembly.

Example 25

The robotic surgical system of any of Examples 21 through 24, wherein the control device is configured to instruct the motor of the robotic arm to continuously supply a predetermined torque to the surgical instrument prior to distally advancing the firing assembly.

Example 26

The robotic surgical system of Example 25, wherein the control device is configured to continuously track an angular position of an output shaft of the motor.

Example 27

The robotic surgical system of Example 26, wherein the control device is configured to measure at least one of a shifting of the shaft or a stretching of the shaft based on the angular position of the output shaft of the motor.

Example 28

The robotic surgical system of Example 27, wherein the control device is configured to adjust an articulation of the end effector based on the at least one of the shifting of the shaft or the stretching of the shaft.

Example 29

The robotic surgical system of any of Examples 26 through 28, wherein the control device is configured to estimate a thickness of the tissue based on the angular position of the output shaft of the motor.

Example 30

The robotic surgical system of Example 29, wherein the control device is configured to modify firing parameters for distally advancing the firing assembly based on the thickness of the tissue.

Example 31

A method of using a surgical instrument (110) comprising: (a) a base (12); (b) a shaft (220) extending distally from the base along a longitudinal axis; (c) an end effector (222) operatively coupled with the shaft, wherein the end effector includes: (i) a first jaw (224), and (ii) a second jaw (226), wherein the second jaw is configured to support a stapling assembly (28); and (d) a firing assembly (280), the method comprising: proximally retracting the firing assembly against at least one of the second jaw or the shaft to thereby apply a compression bias to the shaft; rotating the shaft relative to the base about the longitudinal axis; articulating the end effector relative to the shaft about an articulation joint (267); clamping tissue via the first and second jaws; and distally advancing the firing assembly through the shaft to drive distal translation of a staple actuator of the stapling assembly.

Example 32

The method of Example 31, wherein proximally retracting the firing assembly against at least one of the second jaw or the shaft includes proximally retracting the firing assembly against the second jaw to thereby apply the compression bias to the shaft.

Example 33

The method of Example 31, wherein proximally retracting the firing assembly against at least one of the second jaw or the shaft includes proximally retracting the firing assembly against the shaft to thereby apply the compression bias to the shaft.

Example 34

The method of any of Examples 31 through 33, further comprising continuously maintaining the firing assembly in tension prior to distally advancing the firing assembly.

Example 35

The method of any of Examples 31 through 34, further comprising continuously supplying a predetermined torque to the surgical instrument via a motor prior to distally advancing the firing assembly.

Example 36

The method of Example 35, further comprising continuously tracking an angular position of an output shaft of the motor.

Example 37

The method of Example 36, further comprising measuring at least one of a shifting of the shaft or a stretching of the shaft based on the angular position of the output shaft of the motor.

Example 38

The method of Example 37, further comprising adjusting an articulation of the end effector based on the at least one of the shifting of the shaft or the stretching of the shaft.

Example 39

The method of any of Examples 36 through 38, further comprising estimating a thickness of the tissue based on the angular position of the output shaft of the motor.

Example 40

The method of Example 39, further comprising modifying firing parameters for distally advancing the firing assembly based on the thickness of the tissue.

The following clauses also relate to various non-exhaustive ways in which the teachings herein may be combined or applied.

1. A surgical instrument comprising:
   (a) a base;
   (b) a shaft extending distally from the base along a longitudinal axis, wherein the shaft is configured to rotate relative to the base about the longitudinal axis;
   (c) an end effector operatively coupled with the shaft, wherein the end effector is configured to articulate relative to the shaft about an articulation joint, wherein the end effector includes:
      (i) a first jaw, and
      (ii) a second jaw configured to cooperate with the first jaw to clamp tissue, wherein the second jaw is configured to support a stapling assembly; and
   (d) a firing assembly configured to be distally advanced through the shaft for driving distal translation of a staple actuator of the stapling assembly, wherein the firing assembly is configured to be proximally retracted against at least one of the second jaw or the shaft to thereby apply a compression bias to the shaft.

2. The surgical instrument of Clause 1, wherein the firing assembly is configured to be proximally retracted against the second jaw to thereby apply the compression bias to the shaft.

3. The surgical instrument of Clause 2 wherein the firing assembly includes a knife, wherein the knife is configured to be proximally retracted against the second jaw to thereby apply the compression bias to the shaft.

4. The surgical instrument of Clause 3, wherein the knife includes at least one laterally-outwardly extending wing, wherein the second jaw includes at least one distally-facing hard-stop wall, wherein the at least one laterally-outwardly extending wing knife is configured to be proximally retracted against the at least one distally-facing hard-stop wall to thereby apply the compression bias to the shaft.

5. The surgical instrument of Clause 4, wherein the at least one laterally-outwardly extending wing includes at least one lockout wing.

6. The surgical instrument of Clause 1, wherein the firing assembly is configured to be proximally retracted against the shaft to thereby apply the compression bias to the shaft.

7. The surgical instrument of Clause 6, wherein the firing assembly includes a firing rod, wherein the firing rod is configured to be proximally retracted against the shaft to thereby apply the compression bias to the shaft.

8. The surgical instrument of Clause 7, wherein the firing rod includes a proximally-facing surface, wherein the shaft includes a distally-facing hard-stop wall, wherein the proximally-facing surface is configured to be proximally retracted against the distally-facing hard-stop wall to thereby apply the compression bias to the shaft.

9. The surgical instrument of Clause 8, wherein the firing rod includes a longitudinal slot, wherein the longitudinal slot has a distal slot end defining the proximally-facing surface.

10. The surgical instrument of Clause 8, wherein the shaft includes a protrusion, wherein the protrusion defines the distally-facing hard-stop wall.

11. A robotic surgical system comprising:
   (a) the surgical instrument of Clause 1; and
   (b) a robotic arm having at least one rotatable output configured to distally advance and proximally retract the firing assembly.

12. The robotic surgical system of Clause 11, further comprising a control device configured to instruct a motor of the robotic arm to rotate the at least one rotatable output to distally advance and proximally retract the firing assembly.

13. The robotic surgical system of Clause 12, wherein the control device is configured to instruct the motor of the robotic arm to rotate the at least one rotatable output to proximally retract the firing assembly against the at least one of the second jaw or the shaft to thereby apply the compression bias to the shaft.

14. The robotic surgical system of Clause 13, wherein the control device is configured to instruct the motor of the robotic arm to continuously maintain the firing assembly in tension prior to distally advancing the firing assembly.

15. The robotic surgical system of Clause 13, wherein the control device is configured to instruct the motor of the robotic arm to continuously supply a predetermined torque to the surgical instrument prior to distally advancing the firing assembly.

16. The robotic surgical system of Clause 15, wherein the control device is configured to continuously track an angular position of an output shaft of the motor.

17. The robotic surgical system of Clause 16, wherein the control device is configured to measure at least one of a shifting of the shaft or a stretching of the shaft based on the angular position of the output shaft of the motor.

18. The robotic surgical system of Clause 17, wherein the control device is configured to adjust an articulation of the end effector based on the at least one of the shifting of the shaft or the stretching of the shaft.

19. A robotic surgical system comprising:
   (a) a surgical instrument comprising:
      (i) a base,
      (ii) a shaft extending distally from the base along a longitudinal axis, wherein the shaft is configured to rotate relative to the base about the longitudinal axis,
      (iii) an end effector operatively coupled with the shaft, wherein the end effector is configured to articulate relative to the shaft about an articulation joint, wherein the end effector includes:
         (A) a first jaw, and
         (B) a second jaw configured to cooperate with the first jaw to clamp tissue, wherein the second jaw is configured to support a stapling assembly, and
      (iv) a firing assembly;
   (b) a robotic arm having at least one rotatable output operatively coupled with the firing assembly; and
   (c) a control device configured to:
      (i) instruct a motor of the robotic arm to rotate the at least one rotatable output in a first direction to distally advance the firing assembly through the shaft for driving distal translation of a staple actuator of the stapling assembly, and
      (ii) instruct the motor of the robotic arm to rotate the at least one rotatable output in a second direction to proximally retract the firing assembly against at least one of the second jaw or the shaft to thereby apply a compression bias to the shaft.

20. A method of using a surgical instrument comprising: (a) a base; (b) a shaft extending distally from the base along a longitudinal axis; (c) an end effector operatively coupled with the shaft, wherein the end effector includes: (i) a first jaw, and (ii) a second jaw, wherein the second jaw is configured to support a stapling assembly; and (d) a firing assembly, the method comprising:
   proximally retracting the firing assembly against at least one of the second jaw or the shaft to thereby apply a compression bias to the shaft;
   rotating the shaft relative to the base about the longitudinal axis;
   articulating the end effector relative to the shaft about an articulation joint;
   clamping tissue via the first and second jaws; and
   distally advancing the firing assembly through the shaft to drive distal translation of a staple actuator of the stapling assembly.

VI. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Some versions of the examples described herein may be implemented using a processor, which may be part of a computer system and communicate with a number of peripheral devices via bus subsystem. Versions of the examples described herein that are implemented using a computer system may be implemented using a general-purpose computer that is programmed to perform the methods described herein. Alternatively, versions of the examples described herein that are implemented using a computer system may be implemented using a specific-purpose computer that is constructed with hardware arranged to perform the methods described herein. Versions of the examples described herein may also be implemented using a combination of at least one general-purpose computer and at least one specific-purpose computer.

In versions implemented using a computer system, each processor may include a central processing unit (CPU) of a computer system, a microprocessor, an application-specific integrated circuit (ASIC), other kinds of hardware components, and combinations thereof. A computer system may include more than one type of processor. The peripheral devices of a computer system may include a storage subsystem including, for example, memory devices and a file storage subsystem, user interface input devices, user interface output devices, and a network interface subsystem. The input and output devices may allow user interaction with the computer system. The network interface subsystem may provide an interface to outside networks, including an interface to corresponding interface devices in other computer systems. User interface input devices may include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system.

In versions implemented using a computer system, a storage subsystem may store programming and data constructs that provide the functionality of some or all of the modules and methods described herein. These software modules may be generally executed by the processor of the computer system alone or in combination with other processors. Memory used in the storage subsystem may include a number of memories including a main random-access memory (RAM) for storage of instructions and data during program execution and a read only memory (ROM) in which fixed instructions are stored. A file storage subsystem may provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem in the storage subsystem, or in other machines accessible by the processor.

In versions implemented using a computer system, the computer system itself may be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the example of the computer system described herein is intended only as a specific example for purposes of illustrating the technology disclosed. Many other configurations of a computer system are possible having more or fewer components than the computer system described herein.

As an article of manufacture, rather than a method, a non-transitory computer readable medium (CRM) may be loaded with program instructions executable by a processor.

The program instructions when executed, implement one or more of the computer-implemented methods described above. Alternatively, the program instructions may be loaded on a non-transitory CRM and, when combined with appropriate hardware, become a component of one or more of the computer-implemented systems that practice the methods disclosed.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof are placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:

(a) a base;

(b) a shaft extending distally from the base along a longitudinal axis, wherein the shaft is configured to rotate relative to the base about the longitudinal axis;

(c) an end effector operatively coupled with the shaft, wherein the end effector is configured to articulate relative to the shaft about an articulation joint, wherein the end effector includes:

(i) a first jaw, and (ii) a second jaw configured to cooperate with the first jaw to clamp tissue, wherein the second jaw is configured to support a stapling assembly; and (d) a firing assembly configured to be distally advanced through the shaft for driving distal translation of a staple actuator of the stapling assembly, wherein the firing assembly is configured to be proximally retracted against at least one of the second jaw or the shaft to thereby apply a compression bias to the shaft.

2. The surgical instrument of claim 1, wherein the firing assembly is configured to be proximally retracted against the second jaw to thereby apply the compression bias to the shaft.

3. The surgical instrument of claim 2 wherein the firing assembly includes a knife, wherein the knife is configured to be proximally retracted against the second jaw to thereby apply the compression bias to the shaft.

4. The surgical instrument of claim 3, wherein the knife includes at least one laterally-outwardly extending wing, wherein the second jaw includes at least one distally-facing hard-stop wall, wherein the at least one laterally-outwardly extending wing is configured to be proximally retracted against the at least one distally-facing hard-stop wall to thereby apply the compression bias to the shaft.

5. The surgical instrument of claim 4, wherein the at least one laterally-outwardly extending wing includes at least one lockout wing.

6. The surgical instrument of claim 1, wherein the firing assembly is configured to be proximally retracted against the shaft to thereby apply the compression bias to the shaft.

7. The surgical instrument of claim 6, wherein the firing assembly includes a firing rod, wherein the firing rod is configured to be proximally retracted against the shaft to thereby apply the compression bias to the shaft.

8. The surgical instrument of claim 7, wherein the firing rod includes a proximally-facing surface, wherein the shaft includes a distally-facing hard-stop wall, wherein the proximally-facing surface is configured to be proximally retracted against the distally-facing hard-stop wall to thereby apply the compression bias to the shaft.

9. The surgical instrument of claim 8, wherein the firing rod includes a longitudinal slot, wherein the longitudinal slot has a distal slot end defining the proximally-facing surface.

10. The surgical instrument of claim 8, wherein the shaft includes a protrusion, wherein the protrusion defines the distally-facing hard-stop wall.

11. A robotic surgical system comprising:

(a) the surgical instrument of claim 1; and (b) a robotic arm having at least one rotatable output configured to distally advance and proximally retract the firing assembly.

12. The robotic surgical system of claim 11, further comprising a control device configured to instruct a motor of the robotic arm to rotate the at least one rotatable output to distally advance and proximally retract the firing assembly.

13. The robotic surgical system of claim 12, wherein the control device is configured to instruct the motor of the robotic arm to rotate the at least one rotatable output to proximally retract the firing assembly against the at least one of the second jaw or the shaft to thereby apply the compression bias to the shaft.

14. The robotic surgical system of claim 13, wherein the control device is configured to instruct the motor of the robotic arm to continuously maintain the firing assembly in tension prior to distally advancing the firing assembly.

15. The robotic surgical system of claim 13, wherein the control device is configured to instruct the motor of the robotic arm to continuously supply a predetermined torque to the surgical instrument prior to distally advancing the firing assembly.

16. The robotic surgical system of claim 15, wherein the control device is configured to continuously track an angular position of an output shaft of the motor.

17. The robotic surgical system of claim 16, wherein the control device is configured to measure at least one of a shifting of the shaft or a stretching of the shaft based on the angular position of the output shaft of the motor.

18. The robotic surgical system of claim 17, wherein the control device is configured to adjust an articulation of the end effector based on the at least one of the shifting of the shaft or the stretching of the shaft.

19. A robotic surgical system comprising:

(a) a surgical instrument comprising:

(i) a base, (ii) a shaft extending distally from the base along a longitudinal axis, wherein the shaft is configured to rotate relative to the base about the longitudinal axis, (iii) an end effector operatively coupled with the shaft, wherein the end effector is configured to articulate relative to the shaft about an articulation joint, wherein the end effector includes:

(A) a first jaw, and (B) a second jaw configured to cooperate with the first jaw to clamp tissue, wherein the second jaw is configured to support a stapling assembly, and (iv) a firing assembly;

(b) a robotic arm having at least one rotatable output operatively coupled with the firing assembly; and (c) a control device configured to:

(i) instruct a motor of the robotic arm to rotate the at least one rotatable output in a first direction to distally advance the firing assembly through the shaft for driving distal translation of a staple actuator of the stapling assembly, and (ii) instruct the motor of the robotic arm to rotate the at least one rotatable output in a second direction to proximally retract the firing assembly against at least one of the second jaw or the shaft to thereby apply a compression bias to the shaft.

20. A method of using a surgical instrument comprising: (a) a base; (b) a shaft extending distally from the base along a longitudinal axis; (c) an end effector operatively coupled with the shaft, wherein the end effector includes: (i) a first jaw, and (ii) a second jaw, wherein the second jaw is configured to support a stapling assembly; and (d) a firing assembly, the method comprising:

proximally retracting the firing assembly against at least one of the second jaw or the shaft to thereby apply a compression bias to the shaft;

rotating the shaft relative to the base about the longitudinal axis;

articulating the end effector relative to the shaft about an articulation joint;

clamping tissue via the first and second jaws; and distally advancing the firing assembly through the shaft to drive distal translation of a staple actuator of the stapling assembly.

* * * * *